(12) United States Patent
Miura et al.

(10) Patent No.: US 8,444,953 B2
(45) Date of Patent: May 21, 2013

(54) SYMMETRIC AND ASYMMETRIC HALOGEN-CONTAINING METALLOCARBORANYLPORPHYRINS AND USES THEREOF

(75) Inventors: Michiko Miura, Hampton Bays, NY (US); Haitao Wu, Rockville, MD (US)

(73) Assignee: Brookhaven Science Associates, LLC, Upton, NY (US)

( * ) Notice: Subject to any disclaimer, the term of this patent is extended or adjusted under 35 U.S.C. 154(b) by 1468 days.

(21) Appl. No.: 11/689,678

(22) Filed: Mar. 22, 2007

(65) Prior Publication Data
US 2008/0233047 A1    Sep. 25, 2008

(51) Int. Cl.
*A61K 51/00*    (2006.01)
*A61M 36/14*    (2006.01)

(52) U.S. Cl.
USPC ......................................... 424/1.11; 424/1.65

(58) Field of Classification Search
USPC ....................................................... 424/1.65
See application file for complete search history.

(56) References Cited

U.S. PATENT DOCUMENTS

| | | |
|---|---|---|
| 4,783,529 A | 11/1988 | Lavallee et al. |
| 4,824,659 A | 4/1989 | Hawthorne |
| 4,892,941 A | 1/1990 | Dolphin et al. |
| 4,959,356 A | 9/1990 | Miura et al. |
| 4,977,268 A | 12/1990 | McPhail et al. |
| 5,149,801 A | 9/1992 | Kahl et al. |
| 5,162,231 A | 11/1992 | Cole et al. |
| 5,268,371 A | 12/1993 | Mauclaire et al. |
| 5,312,896 A | 5/1994 | Bhardwaj et al. |
| 5,466,679 A | 11/1995 | Soloway et al. |
| 5,563,132 A | 10/1996 | Bodaness |
| 5,599,796 A | 2/1997 | Schinazi et al. |
| 5,654,423 A | 8/1997 | Kahl et al. |
| 5,672,334 A | 9/1997 | Ranney |
| 5,674,467 A | 10/1997 | Maier et al. |
| 5,679,322 A | 10/1997 | Wilbur |
| 5,707,604 A | 1/1998 | Ranney |
| 5,776,925 A | 7/1998 | Young et al. |
| 5,877,165 A | 3/1999 | Miura et al. |
| 5,955,586 A | 9/1999 | Sessler et al. |
| 6,010,805 A | 1/2000 | Scanlon, Jr. et al. |
| 6,066,628 A | 5/2000 | Stojiljkovic et al. |
| 6,375,930 B2 | 4/2002 | Young et al. |
| 6,566,517 B2 | 5/2003 | Miura et al. |
| 6,759,403 B2 | 7/2004 | Miura et al. |
| 6,765,092 B2 | 7/2004 | Lindsey et al. |
| 6,849,607 B2 | 2/2005 | Pandey et al. |
| 6,906,050 B2 | 6/2005 | Robinson |
| 6,951,640 B2 | 10/2005 | Miura et al. |
| 6,958,389 B2 | 10/2005 | Yano et al. |
| 6,989,443 B2 | 1/2006 | Wu et al. |
| 6,995,260 B2 | 2/2006 | Wu et al. |
| 7,067,653 B2 | 6/2006 | Vicente et al. |
| 7,087,214 B2 | 8/2006 | Bart et al. |
| 2002/0025298 A1 | 2/2002 | Blumenkranz |
| 2004/0019095 A1 | 1/2004 | Xiao et al. |
| 2004/0022734 A1 | 2/2004 | Bourre et al. |
| 2004/0215012 A1 | 10/2004 | Kool et al. |
| 2004/0259810 A1 | 12/2004 | Grierson et al. |
| 2005/0260128 A1* | 11/2005 | Wu et al. .................... 424/1.11 |

FOREIGN PATENT DOCUMENTS

| | | |
|---|---|---|
| WO | WO 01/85736 A1 | 11/2001 |
| WO | WO 2004/030661 | 4/2004 |

OTHER PUBLICATIONS

Fleischer et al. (Inorg. Nucl. Chem. Lett. 1973, 9, 1219-1220).*
Jongwan et al. (Bull. Korean Chem. Soc. 1998, 19, p. 439-444).*
Durantini et al. (Synth. Comm. 1999, 29, 3353-3368).*
E. K. Woller, et al., "2,3,7,8,12,13,17,18-Octafluoro-5,10,15,20-tetraarylporphyrins and Their Zinc Complexes: First Spectroscopic, Electrochemical, and Structural Characterization of a Perfluorinated Tetraarylmetalloporphyrin," *J. Org. Chem.*, 62: 1588-1593 (1997).
K. Prooecinski, et al., "Optical Absorption Study of Porphyrin Agglomeration," http://hermes.umcs.lublin.pl/users/radzki/zad7bw.htm, (2005).
Wu et al., "Total syntheses of three copper (II) tetracarboranylphenylporphyrins containing 40 or 80 boron atoms and their biological properties in EMT-6 tumor-bearing mice," *Biorganic & Medicinal Chemistry*, 14: 5083-5092 (2006).
Morris et al., "Porphyrin-mediated boron neutron capture therapy: evaluation of the reactions of skin and central nervous system," *Int. J. Radiat. Biol.*, 79(3): 149-158 (2003).
Vicente, et al., "Synthesis, dark toxicity and induction of in vitro DNA photodamage by a tetra (4-*nido*-carboranylphenyl)prophyrin," *J. Photochem. Photobiol. B. Biology*, 68(2-3): 123-132 (2002).
Maderna et al., "Synthesis of a porphyrin-labelled carboranyl phosphate diester: a potential new drug for boron neutron capture therapy of cancer," *Chem. Commun.*, 16: 1784-1785 (2002).
Miura et al., "Boron Neutron Capture of a Murine Mammary Carcinoma using a Lipophilic Carboranyltetraphenylporphyrin," *Radiat. Res.*, 155(4): 603-610 (2001).
Miura et al., "Evaluation of carborane-containing porphyrins as tumor targeting agents for boron neutron capture therapy," *Br. J. Radiol.*, 71(847): 773-781 (1998).
Miura et al., "Synthesis of a Nickel Tetracarboranylphenylporphyrin for Boron Neutro-Capture Therapy: Biodistribution and Toxicity in Tumor-Bearing Mice," *Int. J. Cancer*, 68(1): 114-119 (1996).

(Continued)

*Primary Examiner* — Michael G Hartley
*Assistant Examiner* — Melissa Perreira
(74) *Attorney, Agent, or Firm* — Dorene M. Price

(57) ABSTRACT

The present invention is directed to low toxicity boronated compounds and methods for their use in the treatment, visualization, and diagnosis of tumors. More specifically, the present invention is directed to low toxicity halogenated, carborane-containing 5,10,15,20-tetraphenylporphyrin compounds and methods for their use particularly in boron neutron capture therapy (BNCT) and photodynamic therapy (PDT) for the treatment of tumors of the brain, head and neck, and surrounding tissue. The invention is also directed to using these halogenated, carborane-containing tetraphenylporphyrin compounds in methods of tumor imaging and/or diagnosis such as MRI, SPECT, or PET.

9 Claims, No Drawings

OTHER PUBLICATIONS

Kahl et al., "A Carboranyl Porphyrin for Boron Neutron Capture Therapy of Brain Tumors," *Basic Life Sci.*, 50: 193-203 (1989).

Miura et al., "Biodistribution of copper carboranyltetraphenylporphyrins in rodents bearing an isogeneic or human neoplasm," *J. NeuroOncol*, 5: 111-117 (2001).

Berlin et al., "Are Porphyrin Mixtures Favorable Photodynamic Anticancer Drugs? A Model Study with Combinatorial Libraries of Tetraphenylporphyrins," *Combinatorial Chemistry*, 61(2): 107-118 (1998).

Miller et al., "In Vivo Animal Studies with Gadolinium (III) Texaphyrin as a Radiation Enhancer," *Int. J. Radiat. Oncol. Biol. Phys.*, 45(4): 981-989 (1999).

Bhyrappa et al., "Octabromotetraphenylporphyrin and Its Metal Derivatives: Electronic Structure and Electrochemical Properties," *Inorg. Chem.*, 30: 239-245 (1991).

Birnbaum et al., "$^{19}$F NMR Spectra and Structures of Halogenated Porphyrins," *Inorg. Chem.*, 34(14): 3625-3632 (1995).

Fairchild et al., "Current Status of $^{10}$B-Neutron Capture Therapy: Enhancement of Tumor Dose Via Beam Filtration and Dose Rate, and the Effects of These Parameters on Minimum Boron Content: a Theoretical Evaluation," *Int. J. Radiat. Oncol. Biol. Phys.*, 11(4): 831-840 (1985).

Woller et al., "A Straightforward Synthesis of 3,4-Difluoropyrrole," *J. Org. Chem.*, 63(16): 5706-5707 (1998).

Ozette et al., "New Metalloporphyrins with Extremely Altered Redox Properties: Synthesis, Structure, and Facile Reduction to Air-Stable π-Anion Radicals of Zinc and Nickel β-Heptanitroporphyrins," *J. Am. Chem. Soc.*, 119(27): 6442-6443 (1997).

Chanana et al., "Boron Neutron Capture Therapy for Glioblastoma Multiforme: Interim Results from the Phase I/II Dose-Escalation Studies," *Neurosurgery*, 44(6): 1182-1193 (1999).

Vicente et al., "Syntheses of carbon—carbon linked carboranylated porphyrins for boron neutron capture therapy of cancer." *Tetrahedron Letters*, 41: 7623-7627 (2000).

Evstigneeva, "Synthesis of Carboranylporphyrins and the Perspectives of Their Use for Boron Neutron Capture Therapy," *Molecules*, 5: 1479-80 (2001).

Zakharkin et al., "Synthesis of carboranyl derivatives of deuteroporphyrin IX," *Russian Chemical Bulletin*, 48(12): 2312-14 (1999).

Sol, et al., "Synthesis, Spectroscopy, and Photocytotoxicity of Glycosylated Amino Acid Porphyrin Derivatives as Promising Molecules for Cancer Phototherapy," *J. Org. Chem.*, 64: 4431-4444 (1999).

Oulmi, et al., "Glycoconjugated Porphyrins. 3. Synthesis of Flat Amphiphilic Mixed *meso*-(Glycosylated aryl)arylporphyrins and Mixed *meso*-(Glycosylated aryl)alkylporphyrins Bearing Some Mono- and Disaccharide Groups," *J. Org. Chem.*, 60: 1554-1564 (1995).

Sylvain, et al., "Synthesis and Biological Evaluation of Thioglycosylated Porphyrins for an Application in Photodynamic Therapy," *Bioorg Med Chem.*, 10:57-69 (2002).

Frochot, et al., "New Glycosylated Porphyrins for PDT Applications," *Oftalmologia 1*, 56(1):62-6 (2003).

Schell, et al., "Synthesis and Investigation of Glycosylated Mono- and Diarylporphyrins for Photodynamic Therapy," *Bioorg Med Chem.*, 7:1857-1865 (1999).

Kaldapa, et al., "Synthesis of New Glycosylated Neutral and Cationic Porphyrin Dimers," *Tetrahedron Letters*, 4:331-335 (2000).

Bourhim, et al., "Synthesis of New Glycosylated Porphyrin Derivatives with a Hydrocarbon Spacer Arm," *SYNLETT*, 8:563-564 (1993).

Maillard, et al., "Glycoconjugated Porphyrins. 2. Synthesis of Sterically Constrained Polyglycosylated Compounds Derived from Tetraphenylporphyrins," *J. Org. Chem.*, 58:2274-2780 (1993).

Gong, et al., "Amperometric Metronidazole Sensor Based on the Supermolecular Recognition by Metalloporphyrin Incorporated in Carbon Paste Electrode," *Sensors*, 3:91-100 (2003).

Harth et al., "The Effect of Macromolecular Architecture in Nanomaterials: A comparison of Site Isolation in Polyphyrin Core Dedrimers and Their Isomeric Linear Analogues," *J. Am. Chem Soc.* 124: 3926-3938 (2002).

Frixa et al., "Synthesis of meso-substituted porphyrins carrying carboranes and oligo(ethylene glycol) units for potential applications in boron neutron capture therapy," *Org. Biomol. Chem.*, 1: 306-317 (2003).

Foye et al., "Principles of Medicinal Chemistry," Fourth Edition, *Williams and Wilkins*, 902-907 (1995).

Vitale et al., "Boron-Containing Bioactive Molecules: An Approach to Boron Neutron Capture Therapy," *Molecular Medicinal Chemistry*, 8: 1-49 (2005).

Carr et al., "Carborane Complexes of Nickel and Platinum: Synthesis and Protonation Reactions of Anionic Allyl (carborane) Species," *Inorg. Chem.*, 33: 1666-1673 (1994).

Plumb et al., "Tricarbon Carborane Chemistry. 1. Synthesis and Structural Characterizations of Monocage Iron, Manganese, and Nickel Metallatricarbaborane Complexes," *Organometallics*, 11: 1665-1671 (1992).

Teixidor et al., "Macrocycles Incorporating Sulfur and *nido*-Carborane Cages: Reactivity toward Nickel (II) and Palladium (II)," *Inorg. Chem.* 30: 3053-3058 (1991).

Capala et al., "Accumulation of Boron in Malignant and Normal Cells Incubated In Vitro with Boronophenylalanine, Mercaptoborane or Boric Acid," *Radiation Research Society*, 146: 554-560 (1996).

Coderre et al., "Boron neutron capture therapy for glioblastoma multiforme using *p*-boronophenylalanine and epithermal neutrons: Trial design and early clinical results," *Journal of Neuro-Oncology*, 33: 141-152 (1997).

Coderre et al., "Neutron Capture Therapy of the 9L Rat Gliosarcoma Using the *P*-Boronophenylalanine-Fructose Complex," *Int. J. Radiation Oncology Biol. Phys.* 30:(3) 643-652 (1994).

Fairchild et al., "Microanalytical techniques for boron analysis using the $^{10}$B$(n,a)^{7}$Li reaction $^{a)b)}$," *Med. Phys.* 13:(1) 50-56, (1986).

Coderre et al., "Selective Delivery of Boron by the Melanin Precursor Analogue *p*-Boronophenylalanine to Tumors Other Than Melanoma," *Cancer Research*, 50: 138-141 (1990).

Miura et al., "Biodistribution and Toxicity of 2,4-Divinyl-Nido-*o*-Carboranyldeuteroporphyrin IX in Mice," *Biochemical Pharmacology*, 43: 3, 467-476, (1992).

\* cited by examiner

SYMMETRIC AND ASYMMETRIC HALOGEN-CONTAINING METALLOCARBORANYLPORPHYRINS AND USES THEREOF

The present invention was made with government support under Grant No. DE-AC02-98CH10886 awarded by the U.S. Department of Energy. The Government has certain rights in the invention.

BACKGROUND OF THE INVENTION

The efficacy of radiation and chemical methods in the treatment of cancers has been limited by a lack of selective targeting of tumor cells by the therapeutic agent. In an effort to spare normal tissue, current tumor treatment methods have therefore restricted radiation and/or chemical treatment doses to levels that are well below optimal or clinically adequate. Thus, designing compounds that are capable, either alone or as part of a therapeutic method, of selectively targeting and destroying tumor cells, is a field of intense study.

Because of the known affinity of porphyrins to neoplastic tissues, there has been intense interest in using porphyrins as delivery agents in the treatment of neoplasms in brain, head and neck, and related tumors. Porphyrins in general belong to a class of colored, aromatic tetrapyrrole compounds, some of which are found naturally in plants and animals, e.g., chlorophyll and heme, respectively.

Porphyrins and other tetrapyrroles with relatively long singlet lifetimes have already been used to treat malignant tumors using photodynamic therapy (PDT). In PDT, the patient is first injected with a photosensitizing drug, typically a porphyrin. The tumor cells, now photosensitized, are susceptible to destruction when exposed to an intense beam of laser red light. The biochemical mechanism of cell damage in PDT is believed to be mediated largely by singlet oxygen, which is produced by transfer of energy from the light-excited porphyrin molecule to an oxygen molecule. However, PDT has been limited predominantly by the photosensitizing compounds, which have lower than adequate selectivity to tumor cells and higher than optimal toxicity to normal tissue.

A promising new form of cancer therapy is boron neutron-capture therapy (BNCT). BNCT is a bimodal cancer treatment based on the selective accumulation of a stable nuclide of boron, boron-10, or $^{10}$B, in the tumor, followed by irradiation of the tumor with thermalized neutrons. The thermalized neutrons impinge on the boron-10, causing nuclear fission (decay reaction). The nuclear fission reaction causes the highly localized release of vast amounts of energy in the form of high linear-energy-transfer (LET) radiation, which can kill cells more efficiently (higher relative biological effect) than low LET radiation, such as x-rays.

Boron-10 undergoes the following nuclear reaction when captured by a thermal neutron:

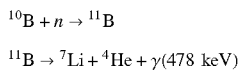

In this nuclear reaction, a boron-10 nucleus captures a neutron forming the metastable nuclide $^{11}$B, which spontaneously and nearly instantaneously disintegrates into a $^{4}$He and $^{7}$Li particle, which together possess an average total kinetic energy of 2.34 MeV. These two ionized particles travel about 9 μm and 5 μm (7±2 μm) in opposite directions in soft tissue, respectively.

The distances traveled by the $^{4}$He and $^{7}$Li particles are comparable to the diameter of many tumor and tumor-associated cells. Therefore, the efficacy of BNCT resides in the production of highly localized, high LET ionizing radiation within the tumor. The targeted tumor thus receives a large dose of radiation while sparing surrounding normal tissue.

In the case of brain tumors, after administration of the boron compound, the patient's head is irradiated in the general area of the brain tumor with an incident beam or field of epithermal (0.5 eV-10 keV) neutrons. The neutrons become progressively thermalized (average energy approximately 0.04 eV) as they penetrate deeper into the head. As the neutrons become thermalized, they are more readily captured by the boron-10 concentrated in the tumor cells and/or tumor supporting tissues, since the capture cross section is inversely proportional to the neutron velocity.

In BNCT, the boron-containing compound must be non-toxic or of low toxicity when administered in therapeutically effective amounts, as well as being capable of selectively accumulating in cancerous tissue. Although p-boronophenylalanine (BPA) has the advantage of low chemical toxicity, it accumulates in critical normal tissues at levels that are less than desirable. In particular, ratios of boron concentration in tumors relative to normal brain and tumors relative to blood are approximately 3:1. Such low specificity limits the maximum dose of BPA to a tumor since the allowable dose to normal tissue is the limiting factor.

A particular class of synthetic porphyrins, known as tetraphenyl porphyrins, have garnered intense interest in the design of new boron carrier compounds for BNCT. Tetraphenylporphyrins (TPPs) contain four phenyl groups on the 5, 10, 15, and 20 positions of the porphyrin ring. An advantage of TPPs is their ease of synthesis.

The solubility of TPPs can be controlled by substituents, generally on the phenyl rings. Those TPPs containing sulfonate or carboxylate substituents are water-soluble. However, some of the carborane-containing TPPs have high lipophilic properties, which can require high amounts of non-aqueous excipients before administration into animals. High amounts of excipients may reduce the biological effect of the porphyrin by, for example, changing the microlocalization within the tumor cell such that the porphyrin may be bound to membranes instead of homogeneously distributed throughout the cell.

In addition, certain substituents such as amide, ester, or urea substituents are subject to hydrolysis. Such hydrolysis is particularly problematic when the substituents are employed to attach the carboranyl group to the porphyrin molecule, since hydrolysis results in loss of the carboranyl group before reaching the target.

Therefore, there continues to be an effort to reduce the lipophilic behavior of TPPs while not compromising their chemical stability. For example, international Patent Application No. WO 01/85736 by Vicente et al describes the synthesis and use of tetraphenylporphyrin compounds that contain hydrophilic carboranyl substituents. A salient feature of the Vicente compounds is the attachment of the carboranyl group to a phenyl ring exclusively by a carbon-carbon linkage. Though the carbon-carbon linkage is not prone to hydrolysis or other chemical attack, the substituent is significantly hydrophobic.

The choice of substituents on the phenyl rings of TPPs may also affect a compound's polarity and ability to target cellular membrane receptors. Various substituents are being studied for improved biodistribution of porphyrin compounds.

A porphyrin molecule has the advantage of having the ability to chelate metal ions in its interior. Such chelated porphyrins can additionally function as visualization tools for real-time monitoring of porphyrin concentration and/or diagnostic agents. For example, when chelated to paramagnetic metal ions, porphyrins may function as contrast agents in magnetic resonance imaging (MRI), and when chelated to radioactive metal ions, porphyrins may function as imaging agents for single photon emission computed tomography (SPECT) or positron emission tomography (PET).

There is a need for new compounds, especially boron-containing porphyrins, that have long retention times in tumors, and that selectively target and destroy tumor cells with minimal damage to normal tissue. In addition, there is a need for more effective methods for the treatment of brain, head and neck, and related tumors, and more particularly, more effective BNCT treatments and boron-delivery compounds used therein.

SUMMARY OF THE INVENTION

The present invention is directed to low toxicity boronated compounds and methods for their use in the treatment, visualization, and diagnosis of tumors. More specifically, the present invention is directed to low toxicity halogen and boron-containing tetraphenylporphyrin compounds and methods for their use particularly in boron neutron capture therapy (BNCT) or photodynamic therapy (PDT) for the treatment of tumors of the brain, head and neck, and surrounding tissue.

In particular, the present invention is directed to halogenated, boronated tetraphenylporphyrins of the formula

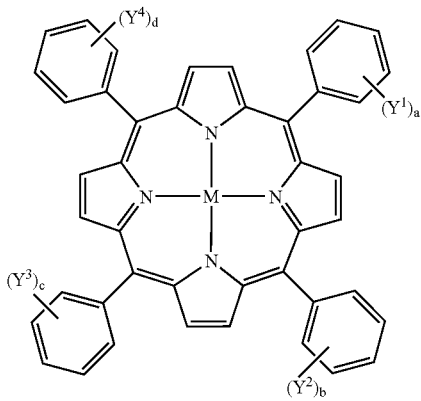

wherein:
$Y^1$, $Y^2$, $Y^3$, and $Y^4$ are independently on one or more of positions of the phenyl ring and are independently hydrogen, hydrocarbyl, non-aromatic carbocyclic, non-aromatic heterocyclic, aryl, alkylaryl, arylalkyl, halogen, alkylhalogen; or a hydrocarbyl, non-aromatic carbocyclic, non-aromatic heterocyclic, aryl, alkylaryl, or arylalkyl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by following formula (2)

$$—X^1—(CR^1R^2)_r—Z \quad (2); and$$

provided that at least one of $Y^1$, $Y^2$, $Y^3$, and $Y^4$ is the substituent represented by formula (2);

Z is a carborane cluster comprising at least two carbon atoms and at least three boron atoms, or at least one carbon atom and at least five boron atoms, within a cage structure, or a substituent represented by the formula

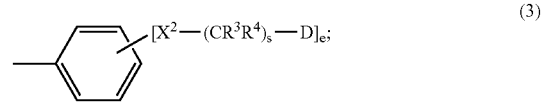

wherein:
$X^1$ and $X^2$ are independently oxygen or sulfur;
$R^1$, $R^2$, $R^3$, $R^4$, $R^5$, $R^6$, $R^7$, $R^8$, and $R^9$ are independently selected from hydrogen and $C_1$ to $C_4$ hydrocarbyl;
r and s are independently 0 or an integer from 1 to 20;
a, b, c, d, and e independently represent an integer from 1 to 5;
D is a carborane cluster comprising at least two carbon atoms and at least three boron atoms, or at least one carbon atom and at least five boron atoms, within a cage structure; and
provided also that at least one of $Y^1$, $Y^2$, $Y^3$, and $Y^4$ is halogen or alkylhalogen; and
M is either two hydrogen ions, a single monovalent metal ion, two monovalent metal ions, a divalent metal ion, a trivalent metal ion, a tetravalent metal ion, a pentavalent metal ion, a hexavalent metal ion, wherein the porphyrin-metal complex derived from a single monovalent metal ion is charge-balanced by a counter cation, and the porphyrin-metal complex derived from a trivalent, tetravalent, pentavalent, or hexavalent metal ion is charge-balanced by an appropriate number of counter anions, dianions, or trianions.

In a preferred embodiment, Z is selected from the carboranes —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

In another preferred embodiment, Z is represented by formula (3) and D is preferably selected from the carboranes —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

M is a radioactive metal ion useful in radioisotope-mediated radiation therapy or imageable by single photon emission computed tomography (SPECT) or positron emission tomography (PET), a paramagnetic metal ion detectable by magnetic resonance imaging (MRI), a metal ion suitable for boron neutron capture therapy (BNCT) or photodynamic therapy (PDT), or a combination thereof.

M is preferably vanadium, manganese, iron, ruthenium, technetium, chromium, platinum, cobalt, nickel, copper, zinc, germanium, indium, tin, yttrium, gold, barium, tungsten, gadolinium or combination thereof. In a more preferred embodiment, M is copper (Cu) or nickel (Ni).

In one embodiment, three of $Y^1$, $Y^2$, $Y^3$, and $Y^4$ are substituents represented by formula (2) wherein the corresponding a, b, c, and d are 1; $R^1$ and $R^2$ are H; X is O; r is 1; Z is closo meta —C$_2$HB$_{10}$H$_{10}$; the $Y^1$—$Y^4$ not represented by formula (2) is fluorine and the corresponding a-d is 2; and said fluorines are on the ortho positions of the phenyl ring.

In another embodiment, three of $Y^1$, $Y^2$, $Y^3$, and $Y^4$ are substituents represented by formula (2) wherein the corresponding a, b, c, and d are 1; $R^1$ and $R^2$ are H; X is O; r is 1; Z is represented by formula (3); $R^3$ and $R^4$ are H; s is 1; D is closo meta —C$_2$HB$_{10}$H$_{10}$; e is 2; the substituents represented by $X^2$—(CR$^3$R$^4$)$_s$-D are in the meta positions of the phenyl ring; the $Y^1$—$Y^4$ not represented by formula (2) is fluorine and the corresponding a-d is 2; and said fluorines are on the ortho positions of the phenyl ring.

In yet another embodiment, when the porphyrin compound requires a counter dianion, the counter dianion is a porphyrin compound containing a divalent negative charge. The porphyrin compound containing a divalent negative charge may be a halogenated carborane-containing porphyrin compound of the present invention, with the proviso that M is absent.

The present invention also includes methods of tumor imaging by SPECT, PET, or MRI, as well as methods of bimodal cancer treatment such as BNCT and PDT that require the administration to a subject of a composition that comprises one or more of the porphyrin compounds described above. In a preferred embodiment, the composition is essentially one or more of the porphyrin compounds as described above.

DETAILED DESCRIPTION OF THE INVENTION

The invention relates to halogenated, boron-containing tetraphenyl porphyrins having the formula

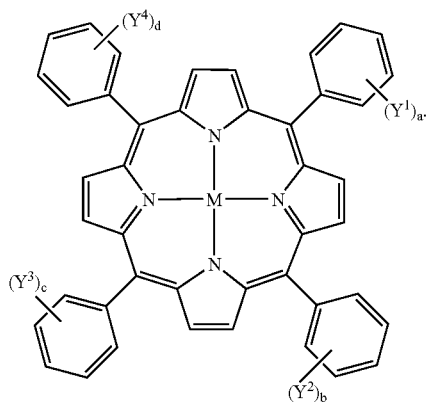

(1)

$Y^1$, $Y^2$, $Y^3$, and $Y^4$ are independently on one or more positions of the phenyl rings, and a, b, c, and d independently represent an integer from 1 to 5.

$Y^1$, $Y^2$, $Y^3$, and $Y^4$ are independently hydrogen, hydrocarbyl, non-aromatic carbocyclic, non-aromatic heterocyclic, aryl, alkylaryl, arylalkyl, halogen, alkylhalogen; or a hydrocarbyl, non-aromatic carbocyclic, non-aromatic heterocyclic, aryl, alkylaryl, or arylalkyl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide, or a substituent represented by formula (2)

$$X^1—(CR^1R^2)_r—Z \quad (2)$$

provided that at least one of $Y^1$, $Y^2$, $Y^3$, and $Y^4$ is the substituent represented by formula (2) and provided that at least one of $Y^1$, $Y^2$, $Y^3$, and $Y^4$ is halogen or alkylhalogen.

In a preferred embodiment, three of $Y^1$, $Y^2$, $Y^3$, and $Y^4$ are represented by formula (2) wherein the corresponding a, b, c, or d are 1; and the $Y^1$—$Y^4$ not represented by formula (2) is represented by a halogen or alkylhalogen and corresponding a, b, c, or d is 2. For example, when $Y^1$, $Y^3$, and $Y^4$ are represented by formula (2), a, c, and d are 1, $Y^2$ is a halogen or alkylhalogen, and b is 2. Alternatively, when $Y^2$, $Y^3$, and $Y^4$ are represented by formula (2), b, c, and d are 1, $Y^1$ is a halogen or alkylhalogen, and a is 2.

In formula (2), $X_1$ is independently oxygen or sulfur. $R^1$ and $R^2$ are independently selected from hydrogen and hydrocarbyl groups as defined below, except that the hydrocarbyl groups for $R^1$ and $R^2$ contain 1 to 4 carbon atoms. The subscript r independently represents 0 or an integer from 1 to 20.

Z is a carborane cluster. A carborane cluster is composed of boron and carbon atoms. Carboranes are polyhedra.

Z comprises at least two carbon atoms and at least three boron atoms, or at least one carbon atom and at least five boron atoms, within a cage structure, or a substituent represented by formula (3).

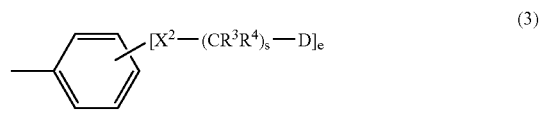

(3)

In formula (3), $X^2$ is independently oxygen or sulfur. $R^3$ and $R^4$ are independently selected from hydrogen and hydrocarbyl groups as defined below, except that the hydrocarbyl groups for $R^3$ and $R^4$ contain 1 to 4 carbon atoms. The subscript s independently represents 0 or an integer from 1 to 20.

D is a carborane cluster. Carborane clusters are described above.

D comprises at least two carbon atoms and at least three boron atoms, or at least one carbon atom and at least five boron atoms, within a cage structure. Some examples of carborane clusters include the regular polyhedral carborane clusters, also known as closo structures, as well as ionized fragments of the polyhedral structures, also known as nido structures. Some examples of the preferred carboranes of the present invention include —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

The halogen can be chlorine, fluorine, bromine, or iodine. The halogen is preferably fluorine.

Alkylhalogen represents one or more halogens bonded to one or more alkyl groups. Some examples of alkylhalogen groups include fluoromethyl, difluoromethyl, 1,2-dichloroethyl, 1-fluoroisobutyl, and 1,3-dibromobutyl.

Hydrocarbyl is a straight chain or branched hydrocarbon group containing 1 to 20 carbon atoms including, optionally, double or triple bonds, preferably up to three double or triple bonds. Some examples of hydrocarbyl groups include methyl, ethyl, n-propyl, iso-propyl, n-butyl, iso-butyl, sec-butyl, tert-butyl, propenyl, 2-butenyl, 3-butenyl, 3-butynyl, 2-methyl-2-butenyl, n-pentyl, dodecyl, hexadecyl, octadecyl, linoleic, and eicosyl.

The hydrocarbyl group may be unsubstituted or substituted with as many hydrophilic groups that the hydrocarbyl group can tolerate, e.g. 1 to 4. Some examples of suitable hydrophilic groups include hydroxy, alkoxy, —C(O)OR$^5$, —SOR$^6$, —SO$_2$R$^6$, nitro, amido, ureido, carbamato, —SR$^7$, —NR$^8$R$^9$, and poly-alkyleneoxide. $R^5$, $R^6$, $R^7$, $R^8$, and $R^9$ are independently selected from hydrogen and hydrocarbyl groups as defined above, except that the hydrocarbyl groups for $R^5$, $R^6$, $R^7$, and $R^8$ contain 1 to 4 carbon atoms.

The carbon atoms of the hydrocarbyl group may also be substituted with 1 to 4 heteroatoms. In this specification, heteroatoms are O, S, N, or NR$^{10}$. where R$^{10}$ is selected from hydrogen and hydrocarbyl groups as defined above. The heteroatoms are generally not adjacent, and are preferably separated from each other by at least one carbon atom. Preferably, there is no more than one heteroatom for each two carbon atoms.

The non-aromatic carbocyclic or heterocyclic ring is a 4, 5, 6, 7, or 8 member carbocyclic or heterocyclic ring. The ring may be saturated, or may contain as many unsaturated (i.e., double or triple) bonds as a carbocyclic ring can tolerate.

Some examples of saturated carbocyclic rings include cyclobutane, cyclopentane, cyclohexane, and cyclopentane rings. Some examples of unsaturated carbocyclic rings include cyclobutene, cyclopentene, cyclohexene, and 1,3-cycloheptadiene rings.

The heterocyclic ring comprises as many heteroatoms, i.e. O, S, N, or $NR^{10}$, as the heterocyclic ring can tolerate, e.g. 1 to 4. Some examples of saturated and unsaturated non-aromatic heterocyclic rings include pyrrolidinyl, piperidine, piperazine, tetrahydrofuran, furan, thiophene, 1,3-oxazolidine, imidazole, and pyrrole rings. The heterocyclic rings may be optionally substituted with hydrocarbyl as defined above, or with 1 to 4 hydrophilic groups, also as defined above.

The non-aromatic carbocyclic or heterocyclic ring may be a bicyclic ring. Some examples of carbocyclic rings are bicyclo[2.2.2.]octane, bicyclo[3.1.1.]heptane, bicyclo[3.3.0.]octane, and bicyclo[4.3.0.]non-3-ene. Examples of non-aromatic heterocyclic rings include 1,4 azabicyclo[2.2.2.]octane and 2-azabicyclo[3.1.1.]heptane.

An aryl group can be either aromatic carbocyclic or aromatic heterocyclic. An aromatic carbocyclic ring is preferably phenyl.

The aryl rings may be optionally substituted with hydrocarbyl as defined above to produce alkylaryl or arylalkyl groups. The aryl, alkylaryl, and arylalkyl groups may be substituted with 1 to 4 hydrophilic groups, as defined above.

Aromatic heterocyclic rings comprise 1 to 4 heteroatoms, i.e. O, S, N, or $NR^{10}$. The rings are typically 5, 6, or 7 member. Some examples of aromatic heterocyclic rings include thiophene, pyridine, oxazole, thiazole, oxazine, and pyrazine rings. The aromatic heterocyclic ring may be substituted with 1 to 4 hydrophilic groups, as defined above.

Any of the above rings may also be fused to 1 to 3 additional 5, 6, or 7 member aryl rings. Some examples of fused rings include napthalene, anthracene, phenanthrene, triphenylene, chrysene, indoline, quinoline, and tetraazanaphthalene (pteridine) rings.

In this specification, an alkoxy group contains a hydrocarbyl portion as defined above. Some examples of alkoxy groups include methoxy, ethoxy, propoxy, n-butoxy, t-butoxy, and dodecyloxy.

A polyalkylene oxide is defined according to the formula $-(CH_2)_d-O-[(CH_2)_e-O-]_x-[(CH_2)_f-O-]_y-(CH_2)_g-OR'$, wherein, independently, d is 0, or an integer from 1 to 10, e is 0, or an integer from 1 to 10, f is 1 to 10, g is 1 to 10, x and y are each independently 1 or 0, and R' is either H or a hydrocarbyl group as defined previously, provided that when e is 0, then x is 0; when f is 0, then y is 0; when e is not 0, then x is 1; and when f is not 0, then y is 1.

A preferable polyalkylene oxide of the invention is polyethylene oxide. Polyethylene oxide is defined according to the formula $-(CH_2)_d-O-[(CH_2)_e-O-]_x-[(CH_2)_f-O-]_y-(CH_2)_g-OR'$, wherein, independently, d is 0 or 2, e is 0 or 2, f is 0 or 2, g is 2, x and y are each independently 1 or 0, and R' is either H or an ethyl group, provided that when e is 0, then x is 0; when f is 0, then y is 0; when e is not 0, then x is 1; and when f is not 0, then y is 1.

In formula (1), M may be two hydrogen ions, a single monovalent metal ion, or two monovalent metal ions. Some examples of suitable monovalent metal ions include $Li^{+1}$, $Na^{+1}$, $K^{+1}$, $Cu^{+1}$, $Ag^{+1}$, $Au^{+1}$, and $Tl^{+1}$. When M is a single monovalent metal ion, the resulting porphyrin-metal complex anion is charge-balanced by a counter cation. Some examples of counter cations include any of the foregoing monovalent metal ions, and ammonium and phosphonium cations, such as tetramethylammonium, tetrabutylammonium, tetraphenylammonium, tetramethylphosphonium, tetrabutylphosphonium, and tetraphenylphosphonium. The counter cation may be either bound or associated in some form with the porphyrin-metal complex.

M may also be a divalent metal ion. Some examples of suitable divalent metal ions include $V^{+2}$, $Mn^{+2}$, $Fe^{+2}$, $Ru^{+2}$, $Co^{+2}$, $Ni^{+2}$, $Cu^{+2}$, $Pd^{+2}$, $Pt^{+2}$, $Zn^{+2}$, $Ca^{+2}$, $Mg^{+2}$, $Sr^{+2}$, and $Ba^{+2}$.

Alternatively, M may be a trivalent, tetravalent, pentavalent, or hexavalent metal ion. Some examples of suitable trivalent metal ions include $Gd^{+3}$, $Y^{+3}$, $In^{+3}$, $Cr^{+3}$, $Ga^{+3}$, $A^{+3}$, $Eu^{+3}$, and $Dy^{+3}$. Some examples of suitable tetravalent metal ions include $Tc^{+4}$, $Ge^{+4}$, $Sn^{+4}$, and $Pt^{+4}$. An example of a suitable pentavalent metal ion is $Tc^{+5}$. Some examples of suitable hexavalent metal ions include $W^{+6}$, $Tc^{+6}$, and $Mo^{+6}$.

The resulting porphyrin-metal complex cation is charge-balanced by an appropriate number of counter anions. The anions may be monoanions, dianions, or trianions. For example, a porphyrin-metal complex cation derived from a trivalent metal ion may be charge-balanced by a single counter monoanion, and such a complex derived from a tetravalent metal ion may, for example, be charge-balanced by a single counter dianion or two counter monoanions, and so on.

Some examples of suitable counter monoanions include chloride, perchlorate, sulfate, nitrate, and tetrafluoroborate. Some examples of suitable counter dianions include oxide, sulfide, or a porphyrin compound containing a divalent negative charge. The porphyrin compound containing a divalent negative charge may be a porphyrin compound of the present invention with the proviso that M is absent. An example of a suitable counter trianion includes phosphate.

The counter monoanion, dianion, or trianion may be either bound or associated in some form with a carborane-containing porphyrin compound of the present invention. The carborane-containing porphyrin compound may also be bound to or associated with neutrally charged molecules, such as molecules of solvation, for example, water, acetonitrile, methanol, and so on.

M may be a radioactive metal ion imageable by single photon emission computed tomography (SPECT) or positron emission tomography (PET). Some examples of radioactive metals suitable for SPECT are $^{67}Cu$, $^{99m}Tc$, $^{111}In$, and those for PET include $^{64}CU$, $^{55}Co$. M may also be a radioactive metal useful as a radiopharmaceutical for therapy. Some examples of radioactive metals suitable for such therapy include $^{90}Y$, $^{188}Re$, $^{67}Cu$ M may also be a paramagnetic metal ion detectable by magnetic resonance imaging (MRI). Some examples of such metals include Mn, Fe, Co, and Gd.

In addition, M may be a metal ion suitable for boron neutron capture therapy (BNCT) or photodynamic therapy (PDT); or a combination thereof. The metal ions suitable for BNCT include those described thus far, with the exclusion of those that are photoactive, such as Zn and Sn. Such photoactive metals, and particularly those with long-lived triplet states, are preferable for PDT. Since the dosage for BNCT is 100 to 1000 times greater than the dosage for PDT, a significant accumulation of photoactive metal in the skin could result if such photoactive metals were used in BNCT. Such an accumulation of photoactive metal may cause biological damage.

The invention also relates to methods of treating tumors. In a preferred embodiment, the method of treating malignant tumors, especially brain tumors, is BNCT. Clinical BNCT for malignant brain tumors was carried out at the Brookhaven National Laboratory Medical Department using p-boronophenylalanine (BPA) as the boron carrier (Chanana et al., *Neurosurgery*, 44, 1182-1192, 1999).

The description of BNCT from the Chanana et al. article is incorporated herein by reference. Those having ordinary skill in the art can readily adapt the method to the compounds of the invention.

In BNCT of malignant brain tumors following the method of the present invention, for example, the patient is first given an infusion of a carborane-containing porphyrin of formula (1), which is highly enriched in boron-10. The carborane-containing porphyrin is then concentrated preferentially in the brain tumor within the effective irradiation volume, which, for brain tumors may be a substantial part of the brain. For example, tumors located in most or all of one hemisphere and some or all of the contralateral hemisphere of the brain can accumulate boronated porphyrins.

The tumor area is then irradiated with thermalized neutrons (primary irradiation), some of which are captured by the boron-10 concentrated in the tumor. The relative probability that the slow-moving thermal neutrons will be captured by the boron-10 nuclide is high compared to the probability of capture by all of the other nuclides normally present in mammalian tissues, provided that boron-10 concentrations in tumor tissues is greater than 30 µg/g.

Since a minuscule proportion of the boron-10 nuclei in and around a tumor undergo the nuclear reaction immediately after capturing a neutron, a high concentration of boron-10 in the targeted tissue is necessary for BNCT to be clinically effective. Therefore, to maximize the concentration of boron-10 in the targeted tissue, the carborane clusters are highly enriched in boron-10. Specifically, the boron in the carborane cluster is enriched to at least 95 atom % in boron-10.

An advantage of the present invention over the prior art for the treatment of cancer is that the boron-containing porphyrins of the present invention selectively accumulate in neoplasms in more preferred ratios than other known boron-containing compounds.

Additionally, the porphyrin compounds of the present invention that have been tested in vivo are non-toxic at theoretically therapeutic effective doses. The higher selectivity and lower toxicity of the halogenated carborane-containing porphyrins of the present invention allow for the selective destruction of tumor tissue with minimal disruption of normal tissues and tissue function when irradiated.

Another advantage of the carborane-containing porphyrins of the present invention is their increased polarity, imparted through the asymmetric configuration of the porphyrins by introduction of the strong electron-withdrawing fluoro groups to the phenyl groups of the porphyrins. Therefore, the microlocalization within the tumor cell may be improved yielding a higher relative biological effect.

In addition, the ether linkages in the carborane-containing porphyrins of the present invention are more polar than carbon-carbon linkages and therefore, provide a further reduction in lipophilicity. At the same time, the ether linkages possess greater resistance to hydrolysis than ester or amide linkages.

To accumulate the requisite amount of a compound of the present invention in a tumor, generally a systemically injected or infused dose of about 10-50 milligrams of boron-10 per kg body weight in a pharmaceutically acceptable carrier is administered to a patient. The carrier may include such commercially available excipients as Cremophor EL, propylene glycol, Tween 80, polyethylene glycol, or liposomes. The compound is administered in one or more doses, the last dose being given between about 1 hour and one week prior to the epithermal neutron irradiation.

The timing of the neutron exposure depends upon the concentration of the porphyrin in the blood, which decreases more rapidly with time than the porphyrin concentration in the tumor. However, the timing of the administration of the halogenated carborane-containing tetraphenylporphyrin depends on various considerations that are well known to those skilled in the art of clinical BNCT, including the pharmacokinetic behavior of the compound, (e.g., the rate of absorption of the compound into the tumor and into the tumor vasculature) and the rate of excretion from and/or metabolism of the compound in the tumor and various other tissues that absorb the compound.

In another preferred embodiment, the method of treating malignant tumors of the present invention is via PDT. PDT is a bimodal cancer treatment based on the selective accumulation of a porphyrin in a tumor, followed by irradiation of the tumor with laser red light. Upon activation with light, an electron of the porphyrin is excited from the singlet ground state to an excited singlet state. The electron then can either return to the singlet ground state with the emission of light causing fluorescence, or it can change its spin via intersystem crossing to the triplet state. In the decay of the triplet back down to the ground state singlet, it can transfer energy to ground state triplet dioxygen, which forms the highly reactive singlet oxygen. Biomolecules that react most readily with singlet oxygen include unsaturated lipids and alpha aminoacid residues, both of which are major constituents of biological membranes. Beyond a certain reversible or repairable threshold, damage to membranes, especially to endothelial cell membranes, can lead to local vascular thrombosis and shutdown of blood circulation.

In using PDT in the present invention, the patient is first given an injection or infusion of a photosensitizing carborane-containing porphyrin of formula (1). Fiber-optic probes are then used to illuminate the tumor tissue. For malignant tumors, it is preferable that the PDT photosensitizers have optical absorbance peaks at sufficiently long wavelengths for maximum penetration to the depth of the tumor.

In a preferred embodiment, the therapeutic treatment of malignant tumors may be augmented by the use of SPECT or PET. In SPECT, the patient is first given an infusion or injection of a compound of formula (1) wherein M is a gamma-emitting radioactive metal ion. The patient's head is then scanned noninvasively and the radionuclide concentration, and hence indirectly, the average boron concentration, in each pixel or voxel representing brain or brain tumor tissue is imaged. Contour lines representing zones of equal boron-10 concentration can thereby be drawn on each image of the brain.

SPECT of the brain is at least one order of magnitude more sensitive to isotopic tracers than is conventional radiography or computerized tomography. In addition, SPECT results, as opposed to results from conventional radiography, can be analyzed to provide quantitative information either in defined volumes or voxels of the brain images, in the concentrations of boron relevant to BNCT treatment planning and implementation. SPECT scanning can indicate the presence of a tumor in the patient, as well as its location in the brain or elsewhere in the body. SPECT scanning is noninvasive, fast, and convenient.

In another preferred embodiment, the therapeutic treatment of malignant tumors may be augmented by the use of MRI. In MRI, a patient is first given an infusion or injection of a solution containing a carborane-containing porphyrin of formula (1) chelated to a suitable paramagnetic metal ion. For a brain tumor, the patient's head is then scanned and the paramagnetic metal ion concentration, and thus, boron concentration in the brain is imaged and quantified. MRI utilizing the compounds of the present invention may permit rapid enhanced targeting and treatment planning for neutron irradiation in BNCT before, during and after infusion when the boronated compound is being redistributed in blood, tumor, and healthy tissue.

The halogenated carboranylporphyrins of the present invention are synthesized through a series of separate steps. Provided below is first, a summary of the synthetic steps required for the preparation of the preferred halogen-containing and carborane-containing porphyrins of the present invention, wherein two of $Y^1$, $Y^2$, $Y^3$, and $Y^4$ are represented by the formula $-X-(CR^1R^2)_r-Z$ (2) and the two not represented by formula (2) are halogen or alkylhalogen. The synthetic summary provides general methods for synthesizing compounds of the invention, and thereby includes several different specific ways to achieve any one synthesis. For example, different starting materials may be used to synthesize the same product. Each starting material may require a different set of reaction conditions such as temperature, reaction time, solvents, and extraction and purification procedures. Those skilled in the art will readily be able to ascertain such reaction conditions.

The specific examples describe a preferred method for synthesizing the compounds of the present invention. The scope of this invention is not to be in any way limited by the examples set forth herein. For example, asymetric halogenated carboranylporphyrin compounds can be synthesized by using a mixture of different benzaldehyde or dibenzaldehyde starting materials and proceeding with a similar synthetic reaction as shown in reaction scheme 8. Different halogen and alkylhalogen starting materials can also be used in Reaction Scheme 8 to create various halogen substituents.

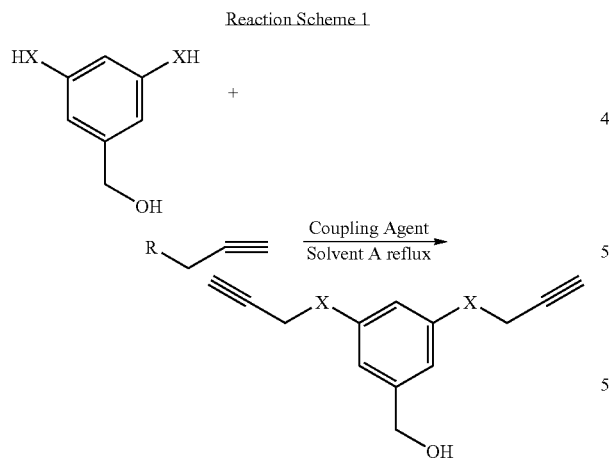

where X is either O or S, R is a halogen, preferably Cl, and solvent A is preferably a polar non-protic solvent such as acetone. The coupling agent is any compound, mixture, or sequence of compounds capable of coupling a phenol or thiophenol and an alkyl halide to produce an ether. Some coupling agents may not require reflux conditions or a polar non-protic solvent. Preferably, the coupling agent is a mixture of potassium carbonate and potassium iodide ($K_2CO_3$/KI).

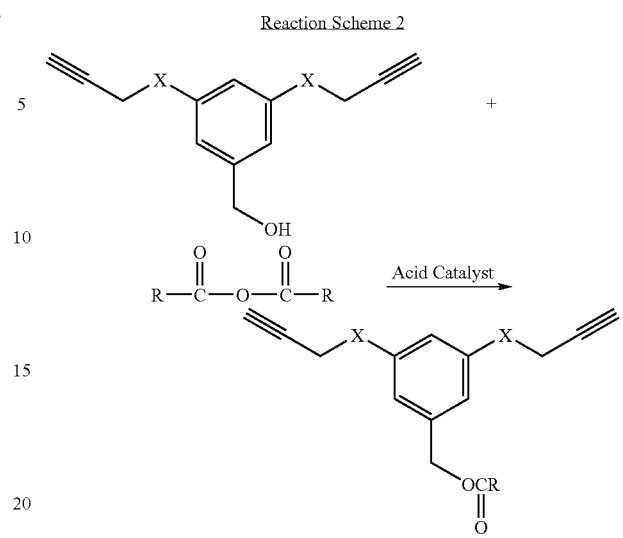

where X is as defined above. The R groups on the anhydride may be the same or different, and selected from hydrocarbyl, non-aromatic carbocyclic, non-aromatic heterocyclic, or aryl. A preferred anhydride is acetic anhydride wherein R is methyl. The acid catalyst may be any Bronsted-Lowry (proton donating) acid that does not interfere with conversion of the alcohol to the ester product. Preferably, the acid catalyst is sulfuric acid, $H_2SO_4$.

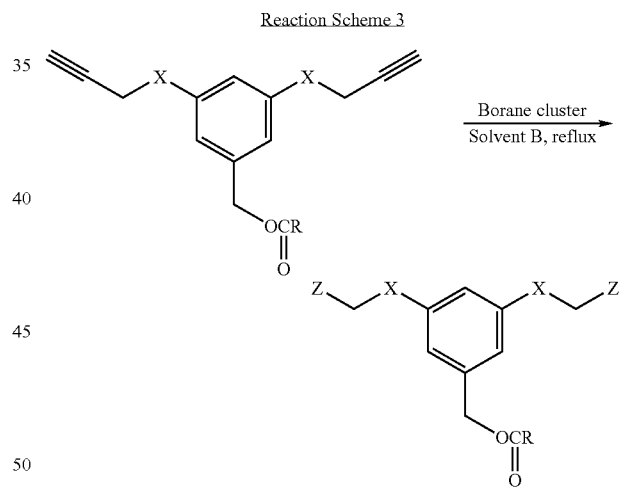

where X and R are as defined above. Solvent B is preferably a polar, aprotic solvent, preferably acetonitrile. The borane cluster is any cluster comprising at least three boron atoms within a cage structure. For example, the borane cluster can be decaborane, $B_{10}H_{14}$. The borane cluster reacts with the triple bond of the propargyl starting material to form the carboranyl product. Thus, in the case of decaborane, Z represents the carborane $-C_2HB_{10}H_{10}$. Z represents any carborane cluster comprising at least two carbon atoms and at least three boron atoms, or at least one carbon atom and at least five boron atoms, within a cage structure. For example, the carborane cluster may be $-C_2HB_9H_{10}$ or $-C_2HB_{10}H_{10}$, wherein $-C_2HB_9H_{10}$ is nido ortho-, meta-, or para-carborane, and $-C_2HB_{10}H_{10}$ is closo ortho-, meta-, or para-carborane.

Reaction Scheme 4

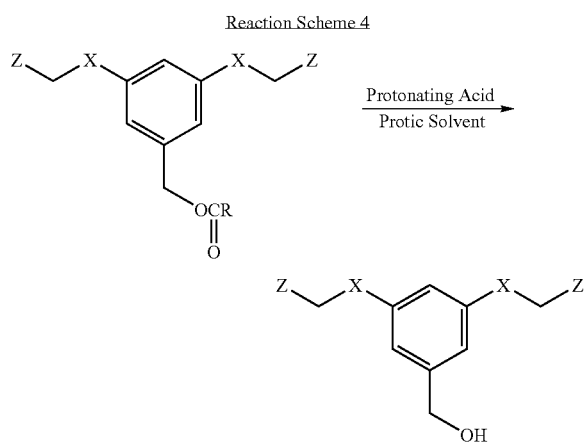

where X, R, and Z are as defined above. The protonating acid is any acid, acid mixture, or sequence of acid additions capable of converting the ester into the alcohol product. Preferably, the protonating acid is concentrated HCl. The protic solvent may be, for example, an alcohol such as methanol.

Reaction Scheme 5

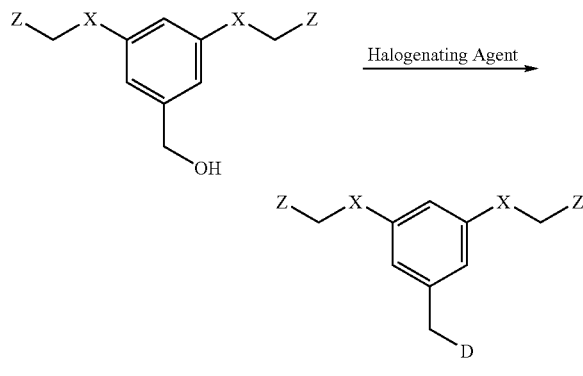

where X and Z are as defined above. D is a halogen. The halogenating agent is any agent capable of converting the hydroxy substituent of the starting material to a halogen. Preferably, the halogenating agent is a 1:1 mixture of carbon tetrabromide and triphenylphosphine, wherein D becomes a bromide. The reaction is performed preferably in an ether solvent, such as tetrahydrofuran (THF).

Reaction Scheme 6

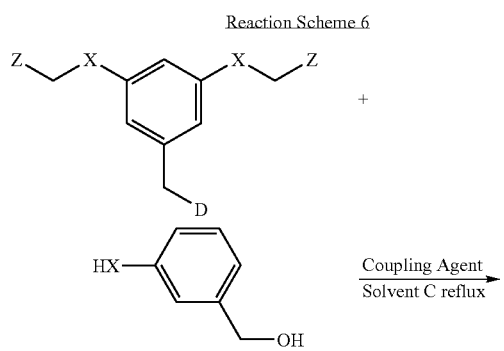

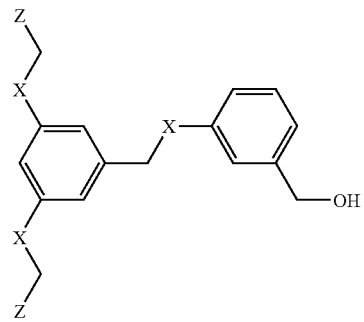

where X, Z, and D are as defined above. Solvent C is preferably a polar, aprotic solvent such as acetone. The coupling agent is any compound, mixture, or sequence of compounds capable of coupling a phenol or thiophenol and an alkyl halide to produce an ether. Some coupling agents may not require reflux conditions or a polar, aprotic solvent. Preferably, the coupling agent is a mixture of potassium carbonate and potassium iodide ($K_2CO_3/KI$).

Reaction Scheme 7

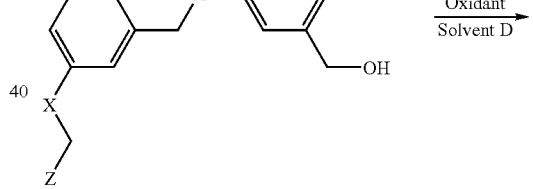

where X and Z are as defined above. The oxidant is any oxidizing compound capable of selectively converting a primary alcohol to an aldehyde, preferably 2,3-dichloro-5,6-dicyano-1,4-benzoquinone (DDQ) or pyridinium chlorochromate (PCC). Solvent D is a non-polar aprotic solvent, preferably dichloromethane.

Reaction Scheme 8

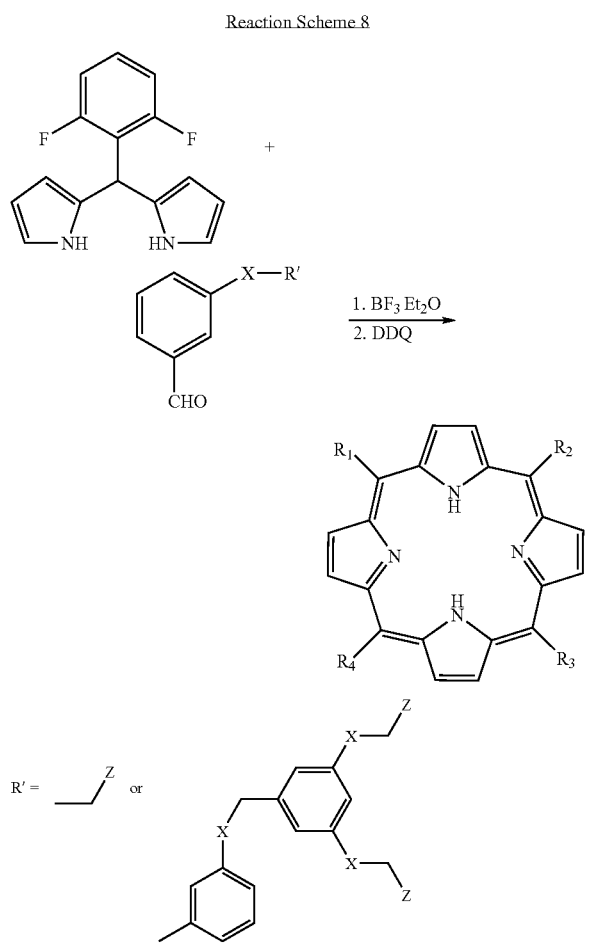

wherein X and Z have been previously defined and R' is defined above. $R_1$, $R_2$, $R_3$, and $R_4$ are independently —X—R' or

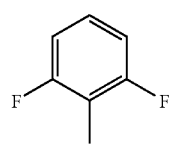

Reaction Scheme 9

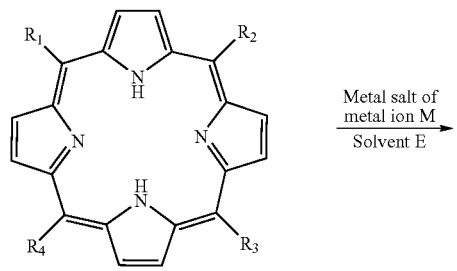

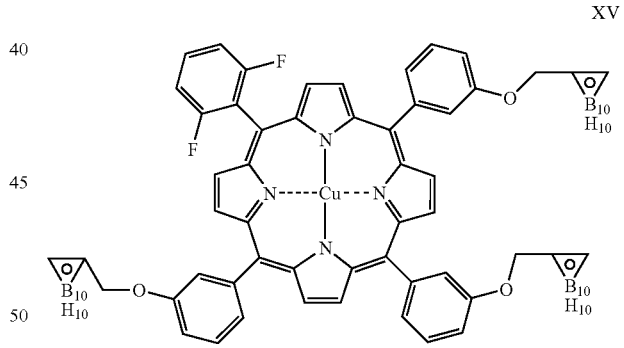

wherein $R_1$, $R_2$, $R_3$, and $R_4$ have been previously defined. In a preferred embodiment, M is selected from the group consisting of vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), and gadolinium (Gd). In a more preferred embodiment, M is copper (Cu) or nickel (Ni). The metal salt used contains the metal ion M chelated to the porphyrin. For example, for the compound where M is desired to be copper, copper acetate, i.e., $Cu(OAc)_2 \cdot H_2O$, may be used as the metal salt. Solvent E is any solvent or solvent mixture capable of at least partially solubilizing the porphyrin and metal salt, and that does not interfere with incorporating the metal into the porphyrin.

For example, using schemes 8-9, and as will be seen through examples 8-11, the 3-carborane-containing porphyrin, i.e., porphyrin (XV), has been prepared. Porphyrin XV has the following structure:

XV

Porphyrin XV shown above. In this case, a, b, and c are 1; $Y^1$, $Y^2$, and $Y^3$ are represented by formula (2); Z is —$C_2HB_{10}H_{10}$ carborane; X is O; r is 1; $R^1$ and $R^2$ are H; $Y^1$, $Y^2$, and $Y^3$ are on the meta position on the phenyl ring; $Y^4$ is F; d is 2; $Y^4$ are on the ortho positions on the phenyl ring; and M is Cu.

EXAMPLES

Examples have been set forth below for the purpose of illustration and to describe the best mode of the invention at the present time. The scope of the invention is not to be in any way limited by the examples set forth herein.

A. Synthesis of 3-[3,5-di(o-carboranylmethoxy)benzyloxy]benzaldehyde (VII)

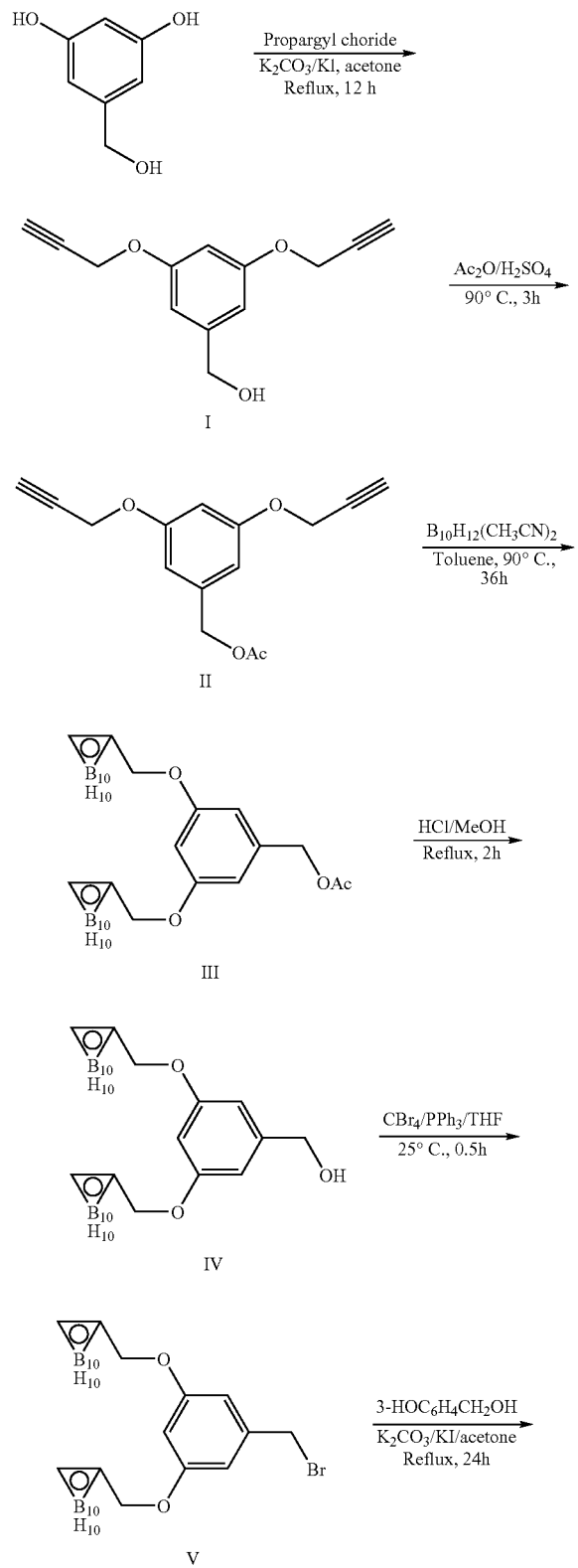

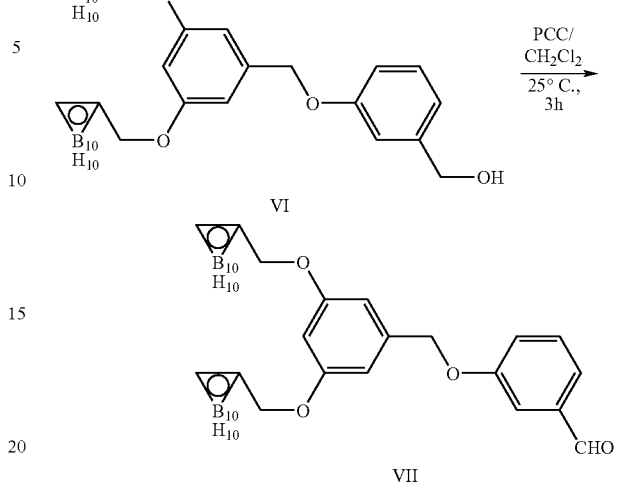

Example 1

Synthesis of 3,5-Dipropargyloxybenzyl alcohol (I)

Finely powdered $K_2CO_3$ (14 g, 0.10 mol), and KI (17 g, 0.10 mol) were stirred in acetone (200 mL) under a nitrogen atmosphere. 3,5-Dihydroxybenzyl alcohol (4.2 g, 0.030 mol), and propargyl chloride (5.3 g, 0.071 mol) were added and mixture was allowed to reflux overnight. After the solution was filtered, and evaporated down to dryness, the residue was diluted with DCM, worked up and the solvents were removed in vacuo leaving a yellow oil, which solidified upon standing to give 6.3 g in 97% yield.

The product had a melting point of 79-80° C. and gave the following proton nuclear magnetic resonance ($^1$H NMR) spectrum in ppm (in $CDCl_3$ solvent): 2.52 (t, 2H, C≡CH); 2.15 (br s, 1H, OH); 4.65 (d, 4H, $ArOCH_2$); 4.60 (s, 2H, $ArH_2$); 6.52 (s, 1H, ArH); 6.60 (s, 2H, ArH). The product gave the following proton-decoupled $^{13}$C NMR spectrum in ppm (in $CDCl_3$ solvent): 56.1 ($ArOCH_2$); 65.1 ($ArCH_2$); 75.9 (C≡C); 78.6 (C≡C); 101.6 (ArC); 106.4 (ArC); 143.8 (ArC); 159.0 (ArC). $C_{13}H_{12}O_3$ requires 216.4, MS (FAB) m/e 217.5 $(M+H)^+$.

Example 2

Synthesis of 3,5-Di(propargyloxy)benzyl acetate (II)

3,5-Dipropargyloxybenzyl alcohol (I) (6.3 g, 0.029 mol) was stirred in acetic anhydride (7 mL, 0.07 mol). Concentrated sulfuric acid (2 drops) was added and the solution was stirred (90-100° C.) for 3 hours. The solution was then poured into ice water, neutralized with a saturated sodium carbonate solution and after the reaction was worked up, the product was purified using silica in a sintered glass funnel and the solvents were removed leaving a yellow oil, which solidified upon standing, 7.2 g in 96% yield.

The product had a melting point of 65-66° C. and gave the following proton nuclear magnetic resonance ($^1$H NMR) spectrum in ppm (in $CDCl_3$ solvent): 2.11 (s, 3H, $CH_3$); 2.54 (t, 2H, C≡CH); 4.67 (d, 4H, $ArOCH_2$); 5.05 (s, 2H, $ArCH_2$); 6.58 (s, 1H, ArH); 6.61 (s, 2H, ArH). The product gave the following proton-decoupled $^{13}$C NMR spectrum in ppm (in CDCl$_3$ solvent): 21.3 (CH$_3$); 56.0 (ArOCH$_2$); 66.2 (ArCH$_2$); 76.2 (C≡C); 78.6 (C≡C); 102.3 (ArC); 108.0 (ArC); 138.8 (ArC); 159.0 (ArC); 171.0 (CO). C$_{15}$H$_{14}$O$_4$ requires 258.3, MS (FAB) m/e 259.5 (M+H)$^+$.

Example 3

Synthesis of 3,5-Di(o-carboranylmethoxy)benzyl acetate (III)

Decaborane (2.70 g, 0.022 mol) was dissolved in dry toluene (80 mL) and stirred at room temperature under a nitrogen atmosphere. Anhydrous acetonitrile (12 mL, 0.22 mol) was added and the solution was stirred for 3 hours. A solution comprised of 3,5-di(propargyloxy)benzyl acetate (II) (2.84 g, 0.011 mol) in toluene (80 mL) was added to the decaborane solution and the mixture was heated to 80-90° C. and was maintained at this temperature for 3 days, after which time the results from analytical thin layer chromatography (TLC) showed no presence of starting material. The excess decaborane was decomposed by the slow addition of methanol (20 mL) while cooling in an ice-water bath. After the solvents were removed by rotary evaporation the resulting residue was dissolved in DCM, washed with 10% sodium bicarbonate, water, dried over anhydrous sodium sulfate and the solvent was removed by rotary evaporation, leaving a yellow oil which crystallized upon standing yielding 4.40 g in 81% yield.

The product had a melting point of 122-123° C. and gave the following proton nuclear magnetic resonance ($^1$H NMR) spectrum in ppm (in CDCl$_3$ solvent): 2.12 (s, 3H, CH$_3$); 4.06 (s, 2H, CCHB$_{10}$H$_{10}$); 4.39 (s, 4H, ArOCH$_2$); 5.01 (s, 2H, ArCH$_2$); 6.32 (s, 1H, ArH); 6.52 (s, 2H, ArH). The product gave the following proton-decoupled $^{13}$C NMR spectrum in ppm (in CDCl$_3$ solvent): 21.4 (CH$_3$); 58.3 (ArOCH$_2$); 65.8 (ArCH$_2$); 69.6 (—CCHB$_{10}$H$_{10}$); 71.5 (—CCHB$_{10}$H$_{10}$); 102.3 (ArC); 108.5 (A$\overline{rC}$); 139.8 (ArC); 158.6 (A$\overline{rC}$); 171.0 (CO). C$_{15}$H$_{34}$O$_{20}$ requires 494.6, MS (FAB) m/e 496.0 (M+H)$^+$.

Example 4

Synthesis of 3,5-Di(o-carboranylmethoxy)benzyl alcohol (IV)

Concentrated HCl (4.0 mL) was added to a solution of 3,5-di(o-carboranylmethoxy)benzyl acetate (III) (4.0 g, 8.0 mmol) in methanol (60 mL) and the mixture was allowed to stir at reflux for 2 hours, after which time TLC showed no starting material. The solvents were then removed leaving a yellow oil, which solidified to a white solid upon standing, 3.4 g, 93% yield.

The product had a melting point of 267-269° C. and gave the following proton nuclear magnetic resonance ($^1$H NMR) spectrum in ppm (in CDCl$_3$ solvent): 2.54 (br s, 1H, OH); 4.04 (s, 2H, CCHB$_{10}$H$_{10}$); 4.40 (s, 4H, ArOCH$_2$); 4.65 (s, 2H, ArCH$_2$); 6.28 (s, 1H, ArH); 6.54 (s, 2H, ArH). The product gave the following proton-decoupled $^{13}$C NMR spectrum in ppm (in CDCl$_3$ solvent): 58.0 (ArOCH$_2$); 64.7 (ArCH$_2$); 69.4 (—CCHB$_{10}$H$_{10}$); 71.3 (—CCHB$_{10}$H$_{10}$); 101.5 (ArC); 106.6 (A$\overline{rC}$); 144.7 (ArC); 158.5 (A$\overline{rC}$). C$_{13}$H$_{32}$O$_{20}$ requires 452.6, MS (FAB) m/e 453.0 (M)$^+$.

Example 5

Synthesis of 3,5-Di(o-carboranylmethoxy)benzylbromide (V)

To a solution of 3,5-di(o-carboranylmethoxy)benzyl alcohol (IV) (0.454 g, 1.0 mmol) and carbon tetrabromide (0.398 g, 1.2 mmol) in a minimal amount of dry THF (~2 mL), triphenylphosphine (0.314 g, 1.2 mmol) was added and the mixture was stirred under argon for 20 min. The reaction mixture was then poured into water and the product extracted with DCM (3×7 mL). The combined extracts were dried with K$_2$CO$_3$ and then purified using a silica pad washed with DCM. The solution was evaporated to dryness yielding a white solid 0.485 g, 92%.

The product had a melting point of 230-232° C. and gave the following proton nuclear magnetic resonance ($^1$H NMR) spectrum in ppm (in CDCl$_3$ solvent): 4.02 (s, 2H, CH), 4.37 (s, 2H, CH$_2$Br), 4.39 (s, 4H, ArOCH$_2$), 6.26 (s, 1H, ArH), 6.55 (s, 2H, ArH). The product gave the following proton-decoupled $^{13}$C NMR spectrum in ppm (in CDCl$_3$ solvent): 32.4 (CH$_2$Br), 58.0 (ArOCH$_2$), 69.5 (—CCHB$_{10}$H$_{10}$), 71.1 (—CCHB$_{10}$H$_{10}$), 102.3 (ArC), 109.2 (A$\overline{rC}$), 141.2 (ArC), and 158.4 (ArC). C$_{13}$H$_{31}$O$_2$B$_{20}$Br requires 515.5, MS (FAB) m/e 516.9 (M+H)$^+$.

Example 6

Synthesis of 3-[3,5-Di(o-carboranylmethoxy)benzyloxy]benzylalcohol (VI)

K$_2$CO$_3$ (0.210 g, 1.5 mmol) and KI (0.25 g, 1.5 mmol) were placed in a 50 mL round-bottom flask. 3,5-Di(o-carboranylmethoxy)benzylbromide (V) (0.410 g, 0.80 mmol), 3-hydroxybenzylalcohol (0.100 g, 0.80 mmol) were dissolved in acetone (20 mL). Under argon the mixture was refluxed for 24 hours. The solvents were evaporated, and the residue was extracted with DC and worked up yielding a white solid, 0.430 g, 96%.

The product had a melting point of 259-261° C. and gave the following proton nuclear magnetic resonance ($^1$H NMR) spectrum in ppm (in CDCl$_3$ solvent): 1.70 (s, 1H, OH), 4.04 (s, 2H, CH), 4.40 (s, 4H, CH$_2$CCHB$_{10}$H$_{10}$), 4.67 (s, 2H, ArCH$_2$OH), 5.00 (s, 2H, ArC$\overline{H_2}$OAr), 6.31 (s, 1H, ArH), 6.60 (s, 2$\overline{H}$, ArH), 6.87 (m, 1H, A$\overline{rH}$), 7.00 (m, 2H, ArH), and 7.26 (m, 1H, ArH). The product gave the following proton-decoupled $^{13}$C NMR spectrum in ppm (in CDCl$_3$ solvent): 58.2 (CH$_2$CCHB$_{10}$H$_{10}$), 65.5 (ArCH$_2$OH), 69.6 (—CCHB$_{10}$H$_{10}$), 71.4 (—CCHB$_{10}$H$_{10}$), 10$\overline{2.0}$ (ArC), 107.4 (A$\overline{rC}$), 113.6 (ArC), 1$\overline{14}$.3 (ArC), 120.2 (ArC), 130.2 (ArC), 141.2 (ArC), 143.1 (ArC), 158.7 (ArC), and 158.8 (ArC). C$_{20}$H$_{38}$O$_4$B$_{20}$ requires 558.7, MS (FAB) m/e 559.0 (M)$^+$.

Example 7

Synthesis of 3-[3,5-di(o-carboranylmethoxy)benzyloxy]benzaldehyde (VII)

Pyridinum chlorochromate (PCC) (0.172 g, 0.80 mmol) was dissolved in 10 mL DCM and cooled in ice water bath. 3-[3,5-Di(o-carboranylmethoxy)benzyloxy]benzylalcohol (VI) (0.223 g, 0.40 mmol), dissolved in 10 mL DCM, was added dropwise to the PCC solution. The mixture was stirred for 2 hours. TLC showed only one new compound. The heterogeneous solution is filtered through a sintered glass funnel containing silica (2 cm). The flask and the silica were washed thoroughly with excess DCM. The solvents were removed, yielding a white solid 0.220 g, 99%.

The product had a melting point of 263-265° C. and gave the following proton nuclear magnetic resonance ($^1$H NMR) spectrum in ppm (in CDCl$_3$ solvent): 4.04 (s, 2H, —CCHB$_{10}$H$_{10}$), 4.42 (s, 4H, ArOCH$_2$), 5.00 (s, 2H, ArCH$_2$O), 6.33 (s, 1H, ArH), 6.61 (s, 2H, ArH), 7.23 (s, 1H, ArH), 7.44 (m, 1H, ArH), 7.50 (m, 2H, ArH), and 9.98 (s, 1H, CHO). The product gave the following proton-decoupled $^{13}$C NMR spectrum in ppm (in CDCl$_3$ solvent): 58.0 (CH$_2$CCHB$_{10}$H$_{10}$), 69.5 (—CCHB$_{10}$H$_{10}$), 69.7 (ArCH$_2$OAr), 71.2 (—CCHB$_{10}$H$_{10}$), 102.0 (ArC), 107.4 (ArC), 112.8 (ArC), 122.4 (ArC), 124.8 (ArC), 130.6 (ArC), 138.1 (ArC), 138.4 (ArC), 140.3 (ArC), 158.6 (ArC), and 192.1 (CHO). C$_{20}$H$_{36}$O$_4$B$_{20}$ requires 556.7, MS (FAB) m/e 558.0 (M+H)$^+$.

B. Synthesis of Copper (II) 5,10,15-tris[3-o-carboranylmethoxyphenyl]-20-[2,6-difluorophenyl]porphyrin (XV) and its analogs

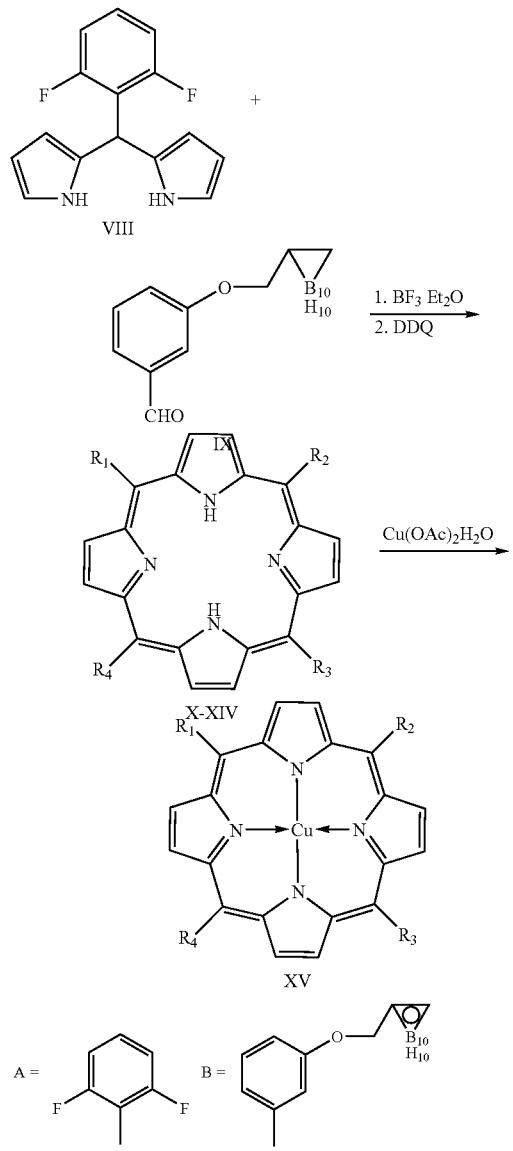

X: R$_1$ = R$_2$ = R$_3$ = R$_4$ = A;
XI: R$_1$ = R$_2$ = R$_3$ = A, R$_4$ = B;
XII: R$_1$ = R$_3$ = A, R$_2$ = R$_4$ = B;
XIII: R$_1$ = A, R$_2$ = R$_3$ = R$_4$ = B;
XIV: R$_1$ = R$_2$ = R$_3$ = R$_4$ = B;
XV: R$_1$ = A, R$_2$ = R$_3$ = R$_4$ = B

Example 8

Synthesis of 2,6-Difluorophenyl dipyrromethane (VIII)

This compound was synthesized using a method described previously [F. Fungo et al, *J Mat Chem*, 2000, 10, 645-650]. Briefly, a solution of freshly distilled pyrrole (17 mL, 0.24 mol) and 2,6-difluorobenzaldehyde (1.4 g, 10 mmol) in dry DCM (20 mL) was bubbled with argon for 20 min. BF$_3$.Et$_2$O (12 µL, 0.5 mmol) was then added. The mixture was stirred at ambient temperature for 1 h. Solvents were removed under vacuum and the residue was dissolved in DCM, and worked up. The product was purified using a silica gel pad eluting with hexane/DCM (2:1, v/v). The yellowish oil solidified upon standing yielding a solid, 2.5 g, 97%. The product was stored in the freezer.

The product gave the following proton nuclear magnetic resonance ($^1$H NMR) spectrum in ppm (in CDCl$_3$ solvent): 5.86 (s, 1H, CH), 5.99 (m, 2H, β-pyr-H), 6.12 (m, 2H, β-pyr-H), 6.61 (m, 2H, α-pyr-H), 6.87 (t, 2H, ArH), 7.16 (m, 1H, ArH), and 8.02 (b, 2H, NH). The product gave the following proton-decoupled carbon-13 nuclear magnetic resonance ($^{13}$C NMR) spectrum in ppm (in CDCl$_3$ solvent): 32.9 (CH), 107.4 (pyr), 108.4 (pyr), 112.0 (ArC), 112.2 (ArC), 117.7 (pyr), 118.0 (ArC), 128.9 (ArC), and 130.1 (pyr).

Example 9

Synthesis of 3-o-Carboranylmethoxybenzaldehyde (IX)

This aldehyde was synthesized using the method described previously. See M. Miura et al, *Tetrahedron Lett.* 1990, 31, 2247-2250.

Example 10

Synthesis of 5,10,15-tris[3-o-carboranylmethoxyphenyl]-20-[2,6-difluorophenyl]porphyrin (XIII) and Its Analogs 3-o-Carboranylmethoxybenzaldehyde (IX) (280 mg, 1.0 mmol) and 2,6-difluorophenyl dipyrromethane (VIII) (258 mg, 1.0 mmol) were placed in a dry 300 mL flask and DCM (100 mL) added via syringe under argon. The solution was deoxygenated by bubbling argon directly into the solution while stirring for 15-20 min. BF$_3$Et$_2$O (12 µL, 0.10 mmol) was added and the solution allowed to stir under an argon atmosphere for about 2 hours. DDQ (227 mg, 1.0 mmol) was added and the reddish brown solution turned dark immediately. The solution was refluxed for one hour. The solvents were removed and the resulting residue was dissolved in a minimum amount of hexane/DCM (1:1) and was eluted through a silica pad. The pale reddish and green by-products eluted first and then DCM was used to elute the reddish brown band. Approximately 265 mg of a red solid was obtained, which TLC showed was a mixture of products. The mixture was separated by preparative TLC using hexane/DCM/acetone (3/2/1 v/v/v) as eluent. The products were identified below according the polarity from high to low: Tetrakis(2,6-fluorophenyl)porphyrin (X); 5-[3-o-carboranylmethoxyphenyl]-10,15,20-tris[2,6-difluorophenyl]porphyrin (XI); 5,15-bis[3-o-carboranylmethoxyphenyl]-10,20-bis[2,6-difluorophenyl]porphyrin (XII); 5,10,15-tris[3-o-carboranylmethoxyphenyl]-20-[2,6-difluorophenyl]porphyrin (XIII); and H$_2$TCPH (XIV).

The reaction yielded 9 mg tetrakis(2,6-fluorophenyl)porphyrin (X). The product gave the following proton nuclear magnetic resonance ($^1$H NMR) spectrum in ppm (in CDCl$_3$ solvent): −2.76 (s, 2H, NH), 7.39 (m, 8H, ArH), 7.80 (m, 4H, ArH), and 8.87 (m, 8H, pyr H). The product gave the following proton-decoupled $^{13}$C NMR spectrum in ppm (in CDCl$_3$ solvent): 120.4 (ArC), 126.9 (ArC), 127.9 (ArC), 134.8 (ArC), 142.4 (pyr C).

The reaction yielded 27 mg 5-[3-o-carboranylmethoxyphenyl]-10,15,20-tris[2,6-difluorophenyl]porphyrin (XI). The product gave the following proton nuclear magnetic resonance ($^1$H NMR) spectrum in ppm (in CDCl$_3$ solvent): −2.73 (s, 2H, NH), 1.71-3.2 (m, 10H, B$_{10}$H$_{10}$), 4.02 (s, 1H, —C CHB$_{10}$H$_{10}$), 4.52 (s, 2H, B$_{10}$H$_{10}$CH$_2$), 7.23 (d-d, 1H, ArH), 7.37 (t, 6H, F—ArH), 7.63 (t, 1H, ArH), 7.71 (m, 1H, ArH), 7.75 (m, 3H, F—ArH), 7.91 (d, 1H, ArH), 8.88 (m, 2H, pyr H), 8.91 (m, 6H, pyr H). The product gave the following proton-decoupled $^{13}$C NMR spectrum in ppm (in CDCl$_3$ solvent): 58.1 (CH$_2$CCHB$_{10}$H$_{10}$), 69.5 (—CCHB$_{10}$H$_{10}$), 71.6 (—CCHB$_{10}$H$_{10}$), 105.6 (ArC), 106.3, 111.4, 111.6, 114.5 (ArC), 119.1, 120.4 (ArC), 121.2 (ArC), 128.1 (ArC), 129.3 (ArC), 131.2 (pyr), 143.8 (ArC), 155.6 (ArC), 161.4 (ArC), and 163.9 (ArC). The ultra-violet visible absorbance spectrum of the product showed the following peaks in nanometers of wavelength (in dichloromethane solvent): 413, 508, 542, 584, and 640.

The reaction yielded 84 mg 5,15-bis[3-o-carboranylmethoxyphenyl]-10,20-bis[2,6-difluorophenyl]porphyrin (XII). The product gave the following proton nuclear magnetic resonance ($^1$H NMR) spectrum in ppm (in CDCl$_3$ solvent): −2.77 (d, 2H, NH), 1.52-3.2 (m, 20H, B$_{10}$H$_{10}$), 4.06 (s, 2H, —CCHB$_{10}$H$_{10}$), 4.54 (s, 4H, B$_{10}$H$_{10}$CH$_2$), 7.25 (m, 2H, ArH), 7.37 (m, 4H, ArH), 7.66 (m, 2H, ArH), 7.71 (m, 2H, ArH), 7.77 (m, 2H, ArH), 7.91 (m, 2H, ArH), 8.87 (m, 4H, pyr H), 8.92 (m, 4H, pyr H). The product gave the following proton-decoupled $^{13}$C NMR spectrum in ppm (in CDCl$_3$ solvent): 58.1 (CH$_2$CCHB$_{10}$H$_{10}$) δ 69.5 (—CCHB$_{10}$H$_{10}$), 71.6 (—CCHB$_{10}$H$_{10}$), 105.5 (ArC), 106.2 (ArC), 111.4 (ArC), 111.6 (ArC), 114.5 (ArC), 119.1 (ArC 1), 120.4 (ArC), 121.2 (ArC), 128.2 (ArC), 129.3 (ArC), 131.2 (ArC), 143.8 (Pyr), 155.6 (ArC), 161.4 (ArC), and 163.9 (ArC). The ultra-violet visible absorbance spectrum of the product showed the following peaks in nanometers of wavelength (in dichloromethane solvent): 414, 510, 543, 586, and 640.

The reaction yielded 64 mg 5,10,15-tris[3-o-carboranylmethoxyphenyl]-20-[2,6-difluorophenyl]porphyrin (XIII). The product had a melting point of 79-80° C. and gave the following proton nuclear magnetic resonance ($^1$H NMR) spectrum in ppm (in CDCl$_3$ solvent): −2.71 (d, 2H, NH), 1.4-3.3 (m, 30H, B$_{10}$H$_{10}$), 4.05 (d, 3H, —CCHB$_{10}$H$_{10}$), 4.46 (d, 6H, B$_{10}$H$_{10}$CH$_2$), 7.06-7.75 (m, 12H, ArH), 8.83 (m, 6H, pyr H), 8.91 (m, 2H, pyr H). The ultra-violet visible absorbance spectrum of the product showed the following peaks in nanometers of wavelength (in dichloromethane solvent): 413, 508, 542, 584, and 640.

The reaction yielded 12 mg H$_2$TCPH (XIV). Product previously described. See M. Miura et al, *Tetrahedron Lett.* 1990, 31, 2247-2250.

Example 11

Synthesis of Copper (II) 5,10,15-tris[3-o-carboranylmethoxyphenyl]-20-[2,6-difluorophenyl]porphyrin (XV)

5,10,15-tris[3-o-carboranylmethoxyphenyl]-20-[2,6-difluorophenyl]porphyrin (XIII) (70 mg, 0.06 mmol) is dissolved in 20 mL methanol, copper acetate (20 mg, 0.10 mmol) is added, reaction took place immediately with the color change from purple to red. The mixture is warmed for 30 min to ensure completion of the reaction. The solvents were removed and the residue was dissolved in hexane/acetone/ethyl acetate: 1:1:1 and then purified on silica pad eluting with the same solvents. Solvents were removed and copper complex, Copper (II) 5,10,15-tris[3-o-carboranylmethoxyphenyl]-20-[2,6-difluorophenyl] porphyrin (XV), was obtained, 65 mg.

The ultra-violet visible absorbance spectrum of the product showed the following peaks in nanometers of wavelength (in acetone solvent): 413, 541.

C. Synthesis of copper (II) 5,15-bis{3-[3,5-di(o-carboranylmethoxy)benzyloxy]phenyl}-10,20-bis[2,6-difluorophenyl]porphyrin (XXI) and Its Analogs

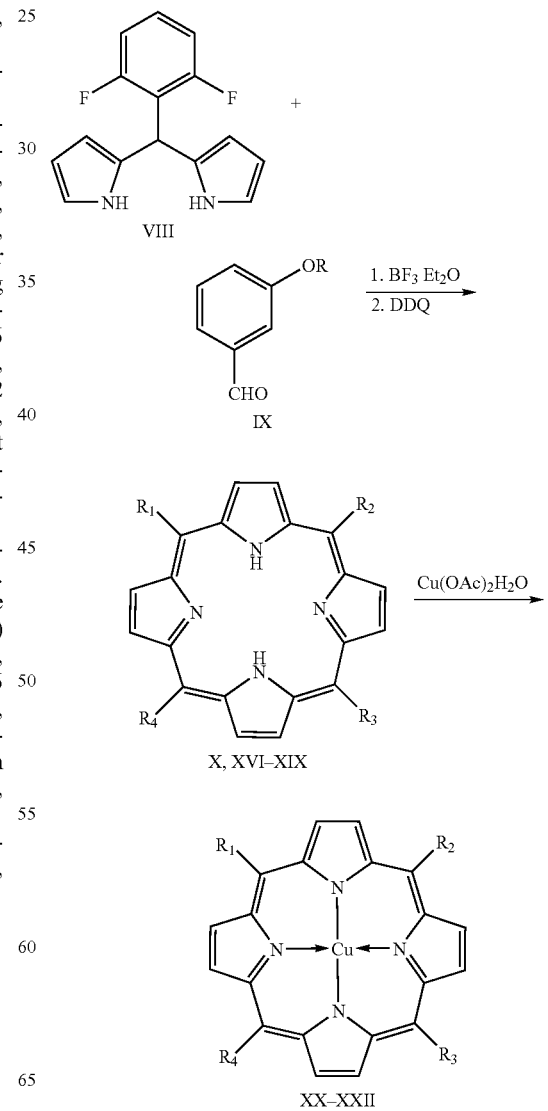

Scheme 3. Synthetic route to free-base porphyrins X, XVI–XIX and copper porphyrin XX–XXII.

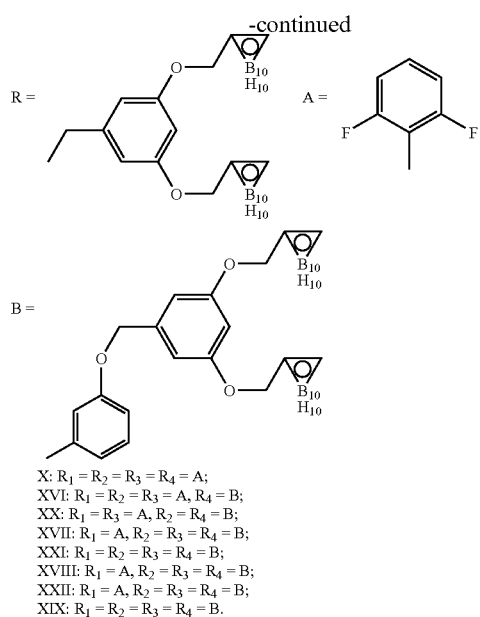

X: $R_1 = R_2 = R_3 = R_4 = A$;
XVI: $R_1 = R_2 = R_3 = A, R_4 = B$;
XX: $R_1 = R_3 = A, R_2 = R_4 = B$;
XVII: $R_1 = A, R_2 = R_3 = R_4 = B$;
XXI: $R_1 = R_2 = R_3 = R_4 = B$;
XVIII: $R_1 = A, R_2 = R_3 = R_4 = B$;
XXII: $R_1 = A, R_2 = R_3 = R_4 = B$;
XIX: $R_1 = R_2 = R_3 = R_4 = B$.

Example 12

Synthesis of 5,15-bis{3-[3,5-di(o-carboranyl-methoxy)benzyloxy]phenyl}-10,20-bis[2,6-difluorophenyl]porphyrin (XVII) and Its Analogs The same procedure was used as in the syntheses of porphyrins X-XIV. See F. Fungo et al, *J Mater. Chem.* 2000, 10, 645-650. The reaction of 3-[3,5-di(o-carboranylmethoxy)benzyloxy]benzaldehyde (VII) (279 mg, 0.5 mmol) and 2,6-difluorophenyl dipyrromethane (VIII) (129 mg, 0.5 mmol) gave 194 mg of a red product mixture. TLC showed two major products and three minor products. These products were separated with preparative TLC using hexane/DCM (3/1, v/v) or hexane/acetone (4/1, v/v) and identified by NMR: meso-tetrakis[2,6-difluorophenyl]porphyrin (X), meso-5-{3-[3,5-di(o-carboranylmethoxy)benzyloxy]phenyl}-10,15,20-tris[2,6-difluorophenyl]porphyrin (XVI), meso-5,15-bis{3-[3,5-di(o-carboranylmethoxy)benzyloxy]phenyl}-10,20-bis[2,6-difluorophenyl]porphyrin (XVII), meso-5,10,15-tris{3-[3,5-di(o-carboranylmethoxy)benzyloxy]phenyl}-20-[2,6-difluorophenyl]porphyrin (XVIII), and meso-tetrakis-{3-[3,5-di(o-carboranylmethoxy)benzyloxy]phenyl}porphyrin (XIX).

The reaction yielded 6 mg meso-tetrakis-{3-[3,5-di(o-carboranylmethoxy)benzyloxy]phenyl}porphyrin (XIX)

The reaction yielded 1 mg meso-5-{3-[3,5-di(o-carboranylmethoxy)benzyloxy]phenyl}-10,15,20-tris[2,6-difluorophenyl]porphyrin (XVI). The product gave the following proton nuclear magnetic resonance ($^1$H NMR) spectrum in ppm (in CDCl$_3$ solvent): −2.77 (s, 2H, NH), 1.31-3.2 (m, 10H, B$_{10}$H$_{10}$), 3.92 (s, 2H, B$_{10}$H$_{10}$CH$_2$), 4.31 (s, 4H, —CCHB$_{10}$H$_{10}$), 5.11 (s, 2H, ArCH$_2$), 6.25 (s, 1H, ArH), 6.60 (s, 2H, ArH), 7.37 (m, 8H, ArH), 7.66 (m, 6H, ArH), 8.83 (m, 2H, pyr-H), 8.87 (m, 6H, pyr-H). The product gave the following proton-decoupled $^{13}$C NMR spectrum in ppm (in acetone-d$_6$ solvent): 61.4 (CH$_2$CCHB$_{10}$H$_{10}$), 70.1 (—CCHB$_{10}$H$_{10}$), 70.2 (ArCH$_2$OAr), 73.8 (—CCHB$_{10}$H$_{10}$), 102.4 (ArC), 106.4 (ArC), 107.2 (ArC), 108.3 (CF), 112.3 (ArC), 112.5 (CF), 115.9 (ArC), 119.0 (ArC), 122.2 (ArC), 122.5 (ArC), 128.7 (ArC), 128.8 (ArC), 132.9 (CF), 141.4 (pyr), 143.6 (pyr), 158.0 (ArC), 159.6 (CF), 162.1 (ArC), 164.6 (ArC). The ultra-violet visible absorbance spectrum of the product showed the following peaks in nanometers of wavelength (in dichloromethane solvent): 413, 509, 541, 583, and 639.

The reaction yielded 87 mg meso-5,15-bis {3-[3,5-di(o-carboranylmethoxy)benzyloxy]phenyl}-10,20-bis[2,6-difluorophenyl]porphyrin (XVII). The product gave the following proton nuclear magnetic resonance ($^1$H NMR) spectrum in ppm (in CDCl$_3$ solvent): −2.74 (d, 2H, NH), 1.31-3.2 (m, 40H, B$_{10}$H$_{10}$), 3.88 (s, 4H, —CCHB$_{10}$H$_{10}$), 4.27 (s, 8H, B$_{10}$H$_{10}$CH$_2$), 5.08 (s, 4H, ArCH$_2$), 6.24 (m, 2H, ArH), 6.57 (m, 4H, ArH), 7.37 (m, 6H, ArH), 7.67 (m, 2H, ArH), 7.78 (m, 4H, ArH), 7.89 (m, 2H, ArH), 8.85 (4H, pyr-H), 8.91 (m, 4H, pyr-H). The product gave the following proton-decoupled $^{13}$C NMR spectrum in ppm (in CDCl$_3$ solvent): 58.0 (CH$_2$CCHB$_{10}$H$_{10}$); 69.3 (—CCHB$_{10}$H$_{10}$); 69.6 (ArCH$_2$OAr); 71.2 (—CCHB$_{10}$H$_{10}$); 101.8 (ArC); 105.3 (ArC); 106.0 (ArC); 107.2 (ArC); 107.2 (ArC); 107.3 (ArC); 111.4 (ArC); 111.7 (ArC); 114.6 (ArC); 114.8 (ArC); 114.9 (ArC); (118.7; 118.9; 119.0; 119.1; 119.3) (ArC); 120.3 (ArC); 121.0 (ArC); 121.6 (ArC); 121.7 (ArC); 128.0 (ArC); 128.4 (ArC); 130.3 (ArC); 131.3 (ArC); 140.6 (ArC); 143.3 (pyr); 143.5 (pyr); 156.9 (ArC); 158.5 (ArC); 161.3 (ArC); 163.8 (ArC). The ultra-violet visible absorbance spectrum of the product showed the following peaks in nanometers of wavelength (in dichloromethane solvent): 415, 510, 544, 585, and 641.0.

The reaction yielded 45 mg meso-5,10,15-tris {3-[3,5-di(o-carboranylmethoxy)benzyloxy]phenyl}-20-[2,6-difluorophenyl]porphyrin (XVIII). The product gave the following proton nuclear magnetic resonance ($^1$H NMR) spectrum in ppm (in CDCl$_3$ solvent): −2.81 (d, 2H, NH), 1.31-3.2 (m, 60H, B$_{10}$H$_{10}$), 3.93 (s, 6H, —CCHB$_{10}$H$_{10}$), 4.33 (s, 12H, B$_{10}$H$_{10}$CH$_2$), 5.15 (s, 6H, ArCH$_2$), 6.28 (m, 3H, ArH), 6.65 (m, 6H, ArH), 7.38 (m, 6H, ArH), 7.69 (m, 2H, ArH), 7.81 (m, 2H, ArH), 7.87 (m, 2H, ArH), 8.85 (m, 6H, pyr-H), 8.91 (m, 2H, pyr-H). The product gave the following proton-decoupled $^{13}$C NMR spectrum in ppm (in CDCl$_3$ solvent): 58.0 (CH$_2$CCHB$_{10}$H$_{10}$), 69.4 (—CCHB$_{10}$H$_{10}$), 69.7 (ArCH$_2$OAr), 71.2 (—CCHB$_{10}$H$_{10}$), 101.9 (ArC), 107.3 (ArC), 111.5 (ArC), 112.9 (ArC), 120.1 (ArC), 120.8 (ArC), 121.6 (ArC), 121.8 (ArC), 122.3 (ArC), 124.6 (ArC), 128.0 (ArC), 128.4 (ArC), 130.5 (ArC), 131.3 (ArC), 138.0 (ArC), 140.1 (CF), 140.7 (CF), 143.4 (pyr), 143.6 (pyr), 156.9 (ArC), 158.5 (ArC), 158.6 (ArC), 159.0 (ArC), 161.4 (ArC), 161.5 (ArC). The ultra-violet visible absorbance spectrum of the product showed the following peaks in nanometers of wavelength (in dichloromethane solvent): 417, 512, 546, 587, and 641.

The reaction yielded 6 mg meso-tetrakis[2,6-difluorophenyl]porphyrin (X).

Example 13

Synthesis of Copper (II) 5,15-bis[3-(3,5-di(o-carboranylmethoxy)benzyloxy)phenyl]-10,20-bis[2,6-difluorophenyl]porphyrin (XX) and its analogs Porphyrins (XVI, XVII, XVIII) were dissolved in 20 mL methanol, copper acetate monohydrate (1.2 mol eq) was added, reaction proceeded immediately with a color change from purple to red. The mixture was warmed (30-40° C.) for 30 min and monitored by optical spectroscopy. After the solvents were removed, the residue was dissolved in dichloromethane and purified on a silica pad eluting with DCM.

The reaction with porphyrin (XVI) yielded 93% copper (II) 5-{3-[3,5-di(o-carboranylmethoxy)benzyloxy]phenyl}-10,15,20-tris[2,6-difluorophenyl]porphyrin (XX). The ultra-violet visible absorbance spectrum of the product showed the following peaks in nanometers of wavelength (in dichloromethane solvent): 411, 536.

The reaction with porphyrin (XVII) yielded 100% copper (II) 5,15-bis{3-[3,5-di(o-carboranylmethoxy)benzyloxy]phenyl}-10,20-bis[2,6-difluorophenyl] (XXI). The ultra-violet visible absorbance spectrum of the product showed the following peaks in nanometers of wavelength (in dichloromethane solvent): 412, 537.

The reaction with porphyrin (XVIII) yielded 86% copper (II) 5,10,15-tris{3-[3,5-di(o-carboranylmethoxy)benzyloxy]phenyl}-20-[2,6-diflurophenyl]porphyrin (XXII). The ultra-violet visible absorbance spectrum of the product showed the following peaks in nanometers of wavelength (in dichloromethane solvent): 413, 538.

Example 14

Preparation of Porphyrin Solutions

Porphyrin compound (XV) was emulsified in 9% Cremophor EL and 18% propylene glycol in saline.

To prepare a solution of ~3.7 mg/mL porphyrin in 9% Cremophor EL (CRM) and 18% propylene glycol (PRG), the porphyrin was dissolved in tetrahydrofuran (THF) (1.5% of the total volume) and then heated to 40° C. for 15 min. CRM (9% of total volume) was then added and the mixture was heated to 60° C., for 2 hours, which removed most of the THF. After cooling to room temperature, PRG (18% of total volume) was added, followed by slow dropwise addition of saline (71.5% of total volume) with rapid stirring. The solution was degassed by stirring under vacuum (~30 mm Hg) for 30-60 min and then filtered (Millipore, 8 μm).

Example 15

Biodistribution of Porphyrin XV in Mice Bearing EMT-6 Carcinomas

BALB/c mice bearing subcutaneously implanted EMT-6 mammary carcinomas implanted on the dorsal thorax were given a total dose of 220 milligrams porphyrin compound XV per kilogram body weight (43 mg B/kg). At one and two days after the last injection, mice were euthanized, and tumor, blood, brain, and liver were removed for boron analyses. The blood was first analyzed for hematologic parameters that indicate toxicity before it was analyzed for boron. Table 1 shows the average boron concentrations for different types of tissue from BALB/c mice.

TABLE 1

Average boron concentrations (μg/g wet tissue) in various tissues in mice (n = 5) given 220 mg/kg porphyrin XV (43 mg B/kg) in 6 i.p. injections over a period of 2 days (3 injections/day given over 8 hours) at either 1 or 2 days after the last injection. Values are reported as median (and range).

| Time after last injection (days) | EMT-6 Tumor (μg B/g) | Blood (μg B/g) | Brain (μg B/g) | Liver (μg B/g) | Skin (pinna) (μg B/g) |
|---|---|---|---|---|---|
| 1 | 66 (24-153) | 47 (38-121) | 1.0 (0.6-1.7) | 300 (245-319) | 5.9 (4.9-9.9) |
| 2 | 88 (44-115) | 0.4 (0.3-4.5) | 0.1 (0-0.2) | 375 (364-419) | 6.6 (3.6-8.1) |

The tumor boron concentrations resulting from a moderate dose of 220 mg/kg porphyrin appear to be very satisfactory, particularly 2 days after the last injection. At day 2, the tumor-to-blood boron ratio has increased tremendously from the previous day. Whereas, the boron concentrations in the brain, skin, and liver are compatible with data from previously tested porphyrins. Since the tumor boron values are high enough at both 1 or 2 days after the injections, the porphyrin compound is likely to be efficacious for BNCT.

Example 16

Weight Changes and Hematologic Parameters from Porphyrin XV

TABLE 2

Weight changes and hematologic parameters in mice given 220 mg/kg porphyrin XV (43 mg B/kg) at 1 or 2 days after the last injection. Values are reported as median (and range).

| Compound | Time after last injection (days) | Number of mice | % Weight change | Platelets | Lymphocytes | Granulocytes |
|---|---|---|---|---|---|---|
| XV | 1 | 5 | −0.6 (−3.4-3.3) | 374 (158-879)[a] | 44.3 (31.8-46.5)[b] | 52 (49.8-65.1) |
| Controls | 1 | 4 | n.d.* | 1127 (1054-1208) | 51.1 (49.1-53.8) | 45.6 (43.5-48.1) |
| XV | 2 | 5 | −0.2 (−3.3-3.8) | 478 (91-661)[b] | 42.6 (38.4-44.1) | 54.0 (52.4-57.8) |
| Controls | 2 | 3 | n.d.* | 898 (831-916) | 32.3 (29.1-66.3) | 65 (28.3-68.3) |

*n.d.—not determined
The Wilcoxon two-sample test with the corresponding control group shows the following differences:
[a]$P < 0.02$,
[b]$P < 0.05$.

The median % weight loss for the mice receiving porphyrin was not significant. Although the platelet count for the mice receiving the porphyrin compound was slightly lower than that of the age-matched control mice, their platelet count rebounded considerably from day 1 to day 2 after the injections. The toxicity from porphyrin XV appears quite mild and transient. Moreover, the dose can likely be increased to some extent without undue toxicity if it is desirable to further increase the tumor boron concentration.

Thus, while the preferred embodiments of the present invention have been described, those skilled in the art will realize that other embodiments can be made without departing from the spirit of the invention, which includes all such further modifications and changes as come within the true scope of the claims set forth herein.

We claim:

1. A compound of the formula

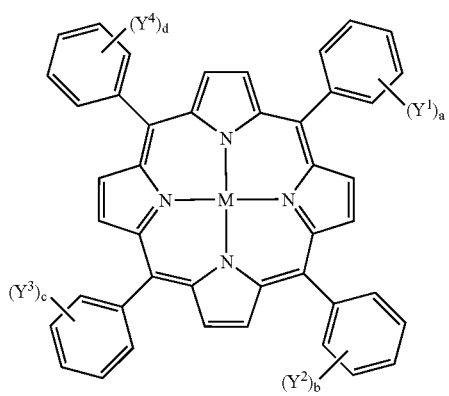

(1)

wherein:
$Y^1$, $Y^2$, $Y^3$, and $Y^4$ are independently on one or more positions of the phenyl rings, and are independently hydrogen, hydrocarbyl, non-aromatic carbocyclic, non-aromatic heterocyclic, aryl, alkylaryl, arylalkyl, halogen, alkylhalogen; or a hydrocarbyl, non-aromatic carbocyclic, non-aromatic heterocyclic, aryl, alkylaryl, or arylalkyl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by formula (2)

—X$^1$—(CR$^1$R$^2$)$_r$—Z    (2); and provided that at least one of $Y^1$, $Y^2$, $Y^3$, and $Y^4$ is the substituent represented by formula (2);

wherein Z is represented by the formula

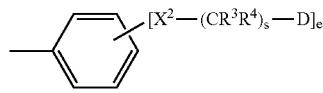

(3)

wherein:
$X^1$ and $X^2$ are independently oxygen or sulfur;
$R^1$, $R^2$, $R^3$, $R^4$, $R^5$, $R^6$, $R^7$, $R^8$, and $R^9$ are independently selected from hydrogen and $C_1$ to $C_4$ hydrocarbyl;
r and s are independently 0 or an integer from 1 to 20;
a, b, c, d, and e independently represent an integer from 1 to 5;

and D is selected from the carboranes —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane and provided also that at least one of $Y^1$, $Y^2$, $Y^3$, and $Y^4$ is halogen or alkylhalogen; and M is either two hydrogen ions, a single monovalent metal ion, two monovalent metal ions, a divalent metal ion, a trivalent metal ion, a tetravalent metal ion, a pentavalent metal ion, a hexavalent metal ion, wherein the porphyrin-metal complex derived from a single monovalent metal ion is charge-balanced by a counter cation, and the porphyrin-metal complex derived from a trivalent, tetravalent, pentavalent, hexavalent metal ion is charge-balanced by an appropriate number of counter anions, dianions, or trianions.

2. The compound according to claim 1 wherein three of $Y^1$, $Y^2$, $Y^3$ and $Y^4$ are substituents represented by formula (2) wherein corresponding a, b, c, and d are 1; and wherein the $Y^1$, $Y^2$, $Y^3$, and $Y^4$ not represented by formula (2) is fluoride, the corresponding a-d is 2, and said fluorides are on the ortho positions of the phenyl ring.

3. The compound according to claim 2 wherein M is vanadium, manganese, iron, ruthenium, technetium, chromium, platinum, cobalt, nickel, copper, zinc, germanium, indium; tin, yttrium, gold, barium, tungsten, gadolinium or combination thereof.

4. The compound according to claim 3 wherein $X^1$ is oxygen; $R^1$ and $R^2$ are hydrogen; and r is 1.

5. The compound according to claim 4 wherein Z is selected from the carboranes —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

6. The compound according to claim 5 wherein the substituents of formula (2) are on the meta positions of each phenyl ring.

7. The compound according to claim 4 wherein Z is represented by formula (3) and D is selected from the carboranes —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

8. The compound according to claim 7 wherein $X^2$ is oxygen, $R^3$ and $R^4$ are hydrogen, s is 1, and e is 2.

9. The compound according to claim 8 wherein the structures —X$^2$—(CR$^3$R$^4$)$_s$-D are in the 3 and 5 positions of each phenyl ring.

* * * * *